(12) United States Patent
Glaser et al.

(10) Patent No.: US 9,557,398 B2
(45) Date of Patent: Jan. 31, 2017

(54) COOPERATIVE PULSES

(75) Inventors: Steffen J. Glaser, Garching (DE); Michael Braun, Munich (DE)

(73) Assignee: Technische Universitaet Muenchen, Munich (DE)

(*) Notice: Subject to any disclaimer, the term of this patent is extended or adjusted under 35 U.S.C. 154(b) by 1079 days.

(21) Appl. No.: 13/704,994

(22) PCT Filed: Jun. 20, 2011

(86) PCT No.: PCT/EP2011/060262
§ 371 (c)(1),
(2), (4) Date: Dec. 18, 2012

(87) PCT Pub. No.: WO2011/161068
PCT Pub. Date: Dec. 29, 2011

(65) Prior Publication Data
US 2013/0090884 A1  Apr. 11, 2013

(30) Foreign Application Priority Data

Jun. 23, 2010  (DE) .......................... 10 2010 024 699

(51) Int. Cl.
*G01R 33/58* (2006.01)
*G06F 17/11* (2006.01)
(Continued)

(52) U.S. Cl.
CPC ......... *G01R 33/583* (2013.01); *G01R 33/4616* (2013.01); *G06F 17/11* (2013.01);
(Continued)

(58) Field of Classification Search
CPC ....... G01N 24/08; G01R 33/441; G01R 33/46; G01R 33/4616; G01R 33/465; G01R 33/583; G06F 17/11
(Continued)

(56) References Cited

U.S. PATENT DOCUMENTS

2010/0264926 A1* 10/2010 Xu ..................... G01R 33/5612
324/313

FOREIGN PATENT DOCUMENTS

JP          4 174 380        6/1992

OTHER PUBLICATIONS

Skinner, Thomas E., et al. "Tailoring the optimal control cost function to a desired output: application to minimizing phase errors in short broadband excitation pulses." Journal of Magnetic Resonance 172.1 (2005): 17-23.*

(Continued)

*Primary Examiner* — Melissa Koval
*Assistant Examiner* — Rishi Patel
(74) *Attorney, Agent, or Firm* — Paul Vincent

(57) ABSTRACT

A method is proposed for the simultaneous optimization of an arbitrary number of electromagnetic pulses, which act in a cooperative way, or mutually compensate each other's errors. The method generally relates to pulses which can have improved properties when cooperating with each other compared to single pulses. In experiments with several scans, undesired signal contributions can be suppressed by COOP pulses, which complements and generalizes the concept of phase cycling. COOP pulses can also be used in individual scans. COOP pulses can be optimized efficiently with the aid of an extended version of the optimal-control-theory-based gradient ascent pulse engineering (GRAPE) algorithm. The advantage of the COOP pulse method is demonstrated theoretically and experimentally for broadband and band-selective excitation and saturation pulses.

17 Claims, 13 Drawing Sheets

(51) Int. Cl.
    *G01N 24/08*    (2006.01)
    *G01R 33/44*    (2006.01)
    *G01R 33/46*    (2006.01)
    *G01R 33/465*   (2006.01)

(52) U.S. Cl.
    CPC ............ *G01N 24/08* (2013.01); *G01R 33/441* (2013.01); *G01R 33/46* (2013.01); *G01R 33/465* (2013.01)

(58) Field of Classification Search
    USPC .................................. 324/300–322; 702/104
    See application file for complete search history.

(56) References Cited

OTHER PUBLICATIONS

Skinner, T. et al., "Application of optimal control theory to the design of broadband excitation pulses for high-resolution NMR" Journal of Magnetic Resonance, Academic Press, Orlando, FL,US, vol. 163, No. 1, Pa. 8-15, Jul. 1, 2003.

Tosner, Z. et al., "Optimal control in NMR spectroscopy: Numerical implementation in SIMPSON", Journal of Magnetic Resonance, Academic Press, Orlando, FL,US vol. 197, No. 2, Pa. 120-134, Dec. 8, 2008.

Levitt, M.H., "Composite Pulses" In: Grant D.M.: "Encyclopedia of Nuclear Magnetic Resonance", John Wiley & Sons, Chichester, vol. 2, Pa. 1396-1411, 1996.

\* cited by examiner

COOPERATIVE PULSES

This application is the national stage of PCT/EP2011/060262 filed on Jun. 20, 2011 and claiming Paris convention of DE 10 2010 024 699.9 filed Jun. 23, 2010.

BACKGROUND OF THE INVENTION

The present invention relates to a method for the simultaneous optimization of an arbitrary number of electromagnetic pulses, which act in a cooperative way, or mutually compensate each other's errors. That is, the invention generally relates to pulses which can have improved properties when cooperating with each other than single pulses. In experiments with several scans, undesired signal contributions can be suppressed by COOP pulses, which complements and generalizes the concept of phase cycling. COOP pulses can be optimized efficiently using an extended version of the optimal-control-based gradient ascent pulse engineering (GRAPE) algorithm. The advantage of the COOP approach is demonstrated experimentally and theoretically for broadband and band-selective excitation and saturation pulses.

It is generally known that radio frequency pulses can influence the system states of spin systems. In this context, according to the present invention, the expression "system state" signifies all physical states a plurality of coupled or uncoupled spins can take. In this context, a system state can be composed of one or several single contributions. Accordingly, Levitt (Prog. Nucl, Magn. Reson. Spectrosc. 18 (1986) 61-122 and in "Encyclopedia of Nuclear Magnetic Resonance", Eds, D. M. Grant and R. K. Harris (Wiley, 1996) and Warren and Silver (Adv. Magn. Reson. 12 (1988) 247-384) describe that in addition to simple rectangular radio-frequency (rf) pulses with constant amplitudes and phases, composite and shaped pulses represent powerful tools for the manipulation of spins in NMR spectroscopy and imaging. In practice, both composite and shaped pulses are implemented as a sequence of rectangular pulses (with different amplitudes and phases). In the following, we will use the generic term "pulse" for both composite or shaped pulses. In the presence of experimental restrictions and errors such as maximum rf amplitudes and rf inhomogeneity, the attainable pulse performance of a pulse is limited by the pulse duration.

Depending on the task of a pulse in an experiment, there are desired and undesired single contributions of the system states. According to the present invention, desired single contributions of the system states are those single contributions of the system states that correspond to the system state demanded by the theory underlying a certain experiment. In contrast thereto, undesired system states are those single contributions of system states that differ from the system state demanded by the theory underlying a certain experiment.

Undesired single contributions to the system state comprise
  phase errors
  signals of nuclei having a certain resonance frequency
    (band selective pulses, solvent signal suppression)
  decoupling sidebands
  signal amplitudes deviating from a desired profile, e.g.
    wherein a desired profile can depend on frequency
    offset and/or the B1 field strength and/or coupling
    constants (comprising scalar coupling, dipolar coupling, quadrupolar coupling) and/or relaxation rates
    (comprising auto relaxation, cross relaxation, autocorrelated relaxation, cross-correlated relaxation) and/or
    diffusion rates and/or chemical exchange rates and/or
    chemical reaction rates and/or spatial coordinates,
    wherein a desired profile can be of any shape, e.g.
    constant signal amplitude, linearly dependent, quadratically dependent signal amplitude, polynomically
    dependent signal amplitude, exponentially or logarithmically dependent signal amplitude, a signal amplitude
    dependent on a random function,
  signals of nuclei with undesired multiplicities
  signals of undesired coherence orders (zero, single,
    double, triple quantum coherences and higher coherence orders)
  signals from undesired coherence transfer pathways
  signals having certain $T_1$ and/or $T_2$ relaxation times
  or
  signals of nuclei having direct coupling to a certain
    isotope (isotope filters).

As an example, referring to a inversion pulse, when starting from equilibrium z magnetization, −z magnetization is a desired system state, all remaining components, for instance components along the +z axis as well as all transverse components are undesired system states in this example. Kobzar et al. (J. Magn. Reson. 170 (2004) 236-243 and J. Magn. Reson. 194, 58-66 (2008)) and Neves et al. (J. Magn. Reson. 181 (2006) 126-134) describe the determination of physical limits of pulse performance using methods of optimal control theory, as it has been described by Bryson and Ho (Applied Optimal Control, Hemisphere, Washington, D.C. (1975)). For example, for a given maximum rf amplitude and a desired bandwidth and robustness with respect to rf inhomogeneity, there exists a minimum pulse duration T* that is required to achieve a desired average fidelity or performance index. It is not possible for a single pulse to compensate its own imperfections to the desired degree if the pulse duration is shorter than T*.

Here, we show that pulse durations can be further reduced by allowing pulses to compensate each other's imperfections. In the following we will refer to this class of cooperatively acting pulses as COOP pulses. In multiscan experiments, for example, imperfections in individual scans are irrelevant if these imperfections cancel in the total accumulated signal. Keeler (Understanding NMR Spectroscopy, Wiley, Chichester, 2005), Bodenhausen et al. (J. Magn. Reson. 58 (1981) 370-388), Bain (J. Magn. Reson. 56 (1984) 418-427) Levitt et al. (J. Magn. Reson. 155 (2002) 300-306) describe phase cycling which is used in many multi-scan experiments for the suppression of artifacts or unwanted signals wherein in each scan, a sequence of identical (shaped) pulses is repeated, except for a systematic phase variation of the pulses (and the receiver). Here, we demonstrate that it is possible to improve the performance of pulse sequences by not only changing the overall phase of a given pulse in subsequent scans, but by cycling through a set of carefully designed COOP pulses which are in general not identical. Khaneja et al. (J. Magn. Reson. 172 (2005) 296-305) and Tosner et al. (J. Magn. Reson. 197 (2009) 120-131) describe the optimal-control-based gradient ascent pulse engineering (GRAPE) algorithm an adapted version of which can be used for optimizing highly compensating COOP cycles.

The optimization of a single (shaped or composite) pulse is usually conducted by the optimal-control-based gradient ascent algorithm GRAPE ("gradient ascent pulse engineering").

Suppose for a given initial magnetization vector M(0) we are looking for a pulse of duration T that optimizes a defined performance index or quality factor φ, wherein we assume for simplicity (but without restricting the generality) that φ depends only on the final magnetization vector M(T). In the case of an excitation pulse, for example, we start with z magnetization, i.e. M(0)=(0, 0, 1)$^t$. Skinner et al. describe (J. Magn. Reson 163 (2003) 8-15) how a simple quality factor can be defined as the x component of the final magnetization. A given pulse is fully characterized by the time-dependent x and y components $v_x(t)=-\gamma B_{rf,x}(t)/2\pi$ and $v_y(t)=-\gamma B_{rf,y}(t)/2\pi$ (or alternatively by the total rf amplitude $v_{rf}(t)=\sqrt{(v_x^2(t)+v_y^2(t))}$ and rf phase $\phi(t)=\tan^{-1}(v_y(t)/v_x(t))$).

The pulse can be improved, if it is known, how the quality factor Φ reacts when the controls $v_x(t)$ and $v_y(t)$ are varied, i.e. if we know the gradients $\delta\Phi/\delta v_x(t)$ and $\delta\Phi/\delta v_y(t)$. These gradients can be approximated using finite differences.

Bryson et al. (Applied Optimal Control, Hemisphere, Wash. D.C. (1975)), Khaneja et al. (J. Magn. Reson. 172 (2005) 296-305), Tosner (J. Magn. Reson. 197 (2009) 120-134), Conolly et al. (IEEE Trans. Med. Imag. MI-5 (1986) 106115) and Skinner et al. (J. Magn. Reson. 163 (2003) 8-1) describe how the same high-dimensional gradients $\delta\Phi/\delta v_x(t)$ and $\delta\Phi/\delta v_y(t)$ can efficiently be calculated to first order based on principles of optimal control theory. This approach requires the calculation of the trajectory of the magnetization vector M(t), and of the so-called costate vector λ(t), for 0≤t≤T. Skinner et al. (J. Magn. Reson. 163 (2003) 8-15; J. Magn. Reson. 167 (2004) 68-74; J. Magn. Reson. 172 (2005) 17-23) describe that the desired gradients are approximated well by the x and y components of the cross product M(t)×λ(t):

$$\frac{\delta\Phi}{\delta v_x(t)} = M_y(t)\lambda_z(t) - M_z(t)\lambda_y(t), \quad (1)$$

$$\frac{\delta\Phi}{\delta v_y(t)} = M_z(t)\lambda_x(t) - M_x(t)\lambda_z(t). \quad (2)$$

For a spin with offset $v_{off}$, the effective field vector $v_e(t)$ is defined as $$v_e(t)=(v_x(t),v_y(t),v_{off})^t, \quad (3)$$

Starting from the initial magnetization vector M(0)=$M_i$, the trajectory of the magnetization vector M(t) can be calculated by solving the Bloch equations $$\dot{M}(t)=2\pi v_e(t)\times M(t). \quad (4)$$

Rourke (Conc. Magn. Reson. 14 (2002) 112-129) describes modifications of the Bloch equations for taking into account relaxation, or radiation damping.

Here, for simplicity we assume that relaxation effects can be neglected, however if necessary they can be taken into account in a straightforward way. Khaneja et al. (J. Magn. Reson. 172 (2005) 296-305) and Gershenzon et al. (J. Magn. Reson. 188 (2007) 330-336) describe how relaxation effects can be taken into account in a straightforward way.

Skinner et al. describe (J. Magn. Reson. 163 (2003) 8-15) that if the pulse performance Φ depends only on the magnetization vector M (T) at the end of the pulse, the costate vector λ(T) is given by ∂Φ/∂M (T), i.e. the three components of the costate vector λ(T)=$(\lambda_x(T), \lambda_y(T), \lambda_z(T))^T$ are $$\lambda_x(T) = \frac{\partial\Phi}{\partial M_x(T)}, \lambda_y(T) = \frac{\partial\Phi}{\partial M_y(T)}, \lambda_z(T) = \frac{\partial\Phi}{\partial M_z(T)}. \quad (5)$$

For example, if the quality factor is simply the projection of the final magnetization vector onto a desired target state F, i.e.

$$\Phi_a=M_x(T)F_x+M_y(T)F_y+M_z(T)F_z, \quad (6)$$

then the final costate vector is simply λ(T)=F. On the other hand, the quality to reach a target state F is defined as $$\Phi_b=1-a_1(M_x(T)-F_x)^2-a_2(M_y(T)-F_y)^2-a_3(M_z(T)-F_z)^2, \quad (7)$$

as has been described by Skinner et al. (J. Magn. Reson. 172 (2005) 17-23), then the resulting final costate vector is given by $\lambda(T)=-(2a_1(M_x-F_x), 2a_2(M_y-F_y), 2a_3(M_z-F_z))^t$. Here, $a_1$, $a_2$ and $a_3$ represent the relative weights given to the desired match of the x, y, and z components of the magnetization vector and the target state. Skinner et al. (J, Magn. Reson. 163 (2003) 8-15; J. Magn. Reson. 167 (2004) 68-74; J. Magn. Reson. 172 (2005) 17-23;) and Gershenzon et al. (J. Magn. Reson. 188 (2007) 330-336) describe that the equation of motion for the costate vector has the same form as the Bloch equations (cf. Eq. (4)), i.e.

$$\dot{\lambda}(t)=2\pi v_e(t)\times\lambda(t), \quad (8)$$

and by propagating λ(T) backward in time we obtain λ(t) for 0≤t≤T.

Khaneja et al. (J. Magn. Reson. 172 (2005) 296-305) and Skinner et al (J. Magn. Reson. 163 (2003) 8-13) describe how robustness with respect to offset and rf inhomogeneity can be achieved by averaging the gradients over all offsets $v_{off}$ and rf scaling factors s of interest. According to the present invention, averaging is to be understood as the calculation of the average value of individual system states, wherein the system states can be considered in the calculation of the average value with different weighting factors which can have both a positive as well as a negative sign and according to the present invention, the average value can be calculated according to the following methods comprising arithmetic, geometric, harmonic, quadratic or cubic averaging:

arithmetic average value: $\bar{x}_{arithm} = \frac{1}{N}\sum_{j=1}^{N} x_j$ geometric average value: $\bar{x}_{geometr} = \sqrt[N]{\sum_{j=1}^{N} x_j}$ harmonic average value: $\bar{x}_{harmon} = \frac{N}{\sum_{j=1}^{N}(x_j^{-1})}$ quadratic average value: $\bar{x}_{quadr} = \sqrt[2]{\frac{1}{N}\sum_{j=1}^{N}(x_j^2)}$ cubic average value: $\bar{x}_{cubic} = \sqrt[3]{\frac{1}{N}\sum_{j=1}^{N}(x_j^3)}$ wherein $x_j$ with j∈{1, 2, . . . , N} corresponds to the elements that are averaged.

Starting from an initial pulse with rf amplitudes $v_x(t)$ and $v_y(t)$, the pulse performance can be optimized by following this averaged gradient. In the simplest approach, the gradient information can be used in steepest ascent algorithms, but faster convergence can often be found using conjugate gradient or efficient quasi-Newton methods that are also based on the gradients $\delta\Phi/\delta v_x(t)$ and $\delta\Phi/\delta v_y(t)$.

The method described above is limited to the optimization of one single pulse at a time.

The technical problem underlying the present invention is to provide an optimization method for being able to simultaneously optimize a group of pulses so that these pulses act in a cooperative manner.

SUMMARY OF THE INVENTION

According to the present invention, this problem is solved by a method for the simultaneous optimization of a group of N electromagnetic pulses $P^{(j)}$ with N>1 wherein the pulses are used to influence system states of a spin system wherein an optimal-control-based algorithm is employed comprising the steps of:

a. selection of N electromagnetic initial pulses $P^{(j)}$ having the duration $T^{(j)}$, with controls $v_x^{(j)}(t)$ and $v_y^{(j)}(t)$ and $j \in \{1, 2, \ldots, N\}$, b. calculation of N trajectories of the system states of the spin system under influence of the pulses $P^{(j)}$ using quantum mechanical equations of motion wherein a given initial state is assumed, respectively, c. Definition of a quality factor (I) that depends at least of the system states at time $T^{(j)}$ and accounts for undesired signal contributions of the system states to be eliminated and for desired single contributions of the system states to be conserved.

d. calculation of costates $\lambda^{(j)}(T^{(j)})$, e. calculation of N trajectories of the costates $\lambda^{(j)}(t)$ for $0 \leq t \leq T^{(j)}$, f. calculation of the gradients of the quality factor $\phi$ with respect to the controls $v_x^{(j)}(t)$ and $v_y^{(j)}(t)$ for an arbitrary number of points in time t, g. addition of the optionally scaled gradients to the controls $v_x^{(j)}(t)$ and $v_y^{(j)}(t)$ whereupon updated controls $v_x^{(j)}(t)$ and $v_y^{(j)}(t)$ are obtained, h. repetition of steps b-g using the updated controls $v_x^{(j)}(t)$ and $v_y^{(j)}(t)$ until a defined abortion criterion is fulfilled.

Preferably, in step f the gradients of the quality factor $\Phi$ are calculated at each point in time t.

An especially simple variant is characterized in that the system states of the spin systems are described by the magnetization vectors $M^{(j)}(t)$, so that in step b the trajectories of the magnetization vectors $M^{(j)}(t)$ are calculated by using the Bloch equations for $0 \leq t \leq T$, the quality factor $\Phi$ depends on the final magnetization vectors $M^{(j)}(T^{(j)})$, in step e, the calculation of the trajectories of the costate vectors $\lambda^{(j)}(t)$ for $0 \leq t \leq T^{(j)}$ is carried out while using the equations of motion for the costate vectors according to $$\dot{\lambda}(t) = 2\pi v_e(t) \times \lambda(t) \quad (9)$$

and in step f, the calculation of the gradients of the quality factor $\Phi$ is carried out by calculation of the x and y components of the vector product $M^{(j)}(t) \times \lambda^{(j)}(t)$:

$$\frac{\delta \Phi}{\delta v_x^{(j)}(t)} = M_y^{(j)}(t) \lambda_z^{(j)}(t) - M_z^{(j)}(t) \lambda_y^{(j)}(t) \quad (10)$$

$$\frac{\delta \Phi}{\delta v_y^{(j)}(t)} = M_z^{(j)}(t) \lambda_x^{(j)}(t) - M_x^{(j)}(t) \lambda_z^{(j)}(t) \quad (11)$$

An alternative variant is characterized in that the system states are described using the density operator formalism or the product operator formalism or modifications of these formalisms for the consideration of relaxation or radiation damping.

The gradient information calculated in step f can be applied in algorithms using the method of steepest ascent.

As an alternative thereto, the gradients calculated in step f can be scaled by using a conjugated gradient method or a quasi Newton method and in step g, these scaled gradients are added to the controls $v_x^{(j)}(t)$ and $v_y^{(j)}(t)$.

A special variant is characterized in that the pulses in subsequent scans are to be applied at the same position of the pulse sequence and the quality factor $\Phi$ depends on the average value of the system states. In doing so, the contributions of the scans to the average value of the system states can be weighted.

Another special variant is characterized in that the pulses in a single scan are to be applied at different positions of a pulse sequence, and the system states are symmetrical with respect to an axis in the transverse plane.

Here, it is advantageous when the axis of symmetry in the transverse plane has a uniform phase or a phase that linearly depends on the offset.

The pulses $P^{(j)}$ preferably are pulses that generate transverse magnetization.

Preferably, the quality factor (P depends only on the final system states.

The method of the present invention is particularly advantageous, when the pulses serve for the manipulation of system states of coupled spin systems.

Preferably, the pulses are heteronuclear or homonuclear decoupling pulses for the suppression of heteronuclear or homonuclear coupling evolution.

In a preferred embodiment, the decoupling pulses are divided into $N_{acq}$ acquisition points, respectively, and the quality factor $\Phi$ depends on the system states at the times $T_k$ of the $N_{acq}$ acquisition points of all N pulses.

Different decoupling pulses can be intended in subsequent scans.

The method according to the present invention is preferably used in the field of NMR spectroscopy, MRI, electron spin resonance spectroscopy and in optical spectroscopy.

According to the present invention, first, for a group of N arbitrarily chosen individual pulses P having a duration T (wherein the method is not restricted to pulses $P^{(j)}$ of equal durations $T^{(j)}$), having rf amplitudes $v_x^{(j)}(t)$ and $v_y^{(j)}(t)$ and $j \in \{1, 2, \ldots, N\}$, wherein a given initial state $M^{(1)}(0) = M^{(2)}(0) = \ldots M^{(N)}(0) = M_t$ (wherein the method is not restricted to identical initial states $M^{(j)}(0)$) is supposed, the corresponding N trajectories (=course in time) $M^{(j)}(t)$ of the magnetization vectors experiencing the effects of the pulses $P^{(j)}$ are calculated using the Bloch equations for $0 \leq t \leq T$, wherein, depending on the final magnetization vectors $M^{(j)}(T)$, a quality factor $\Phi$ (the dependency of which is not restricted to the final magnetization vectors $M^{(j)}(T)$) is defined, so that the costate vectors $\lambda^{(j)}(T)$ are given by $$\lambda_x^{(j)}(T) = \frac{\partial \Phi}{\partial M_x^{(j)}(T)}, \lambda_y^{(j)}(T) = \frac{\partial \Phi}{\partial M_y^{(j)}(T)}, \lambda_z^{(j)}(T) = \frac{\partial \Phi}{\partial M_z^{(j)}(T)}, \quad (12)$$

whereupon the N trajectories $\lambda^{(j)}(t)$ for $0 \leq t \leq T$ are calculated by using the equations of motion for the costate vectors according to equation (8), whereupon the gradients of the quality factor $\Phi$, as it has been described by Skinner et al. (J. Magn. Reson 163 (2003) 8-15), are calculated with respect to the controls $v_x^{(j)}(t)$ and $v_y^{(j)}(t)$ at every point i time by calculating the x and y components of the vectors $M^{(j)}(t) \times \lambda^{(j)}(t)$:

$$\frac{\delta\Phi}{\delta v_x^{(j)}(t)} = M_y^{(j)}(t)\lambda_z^{(j)}(t) - M_z^{(j)}(t)\lambda_y^{(j)}(t) \qquad (13)$$

$$\frac{\delta\Phi}{\delta v_y^{(j)}(t)} = M_z^{(j)}(t)\lambda_x^{(j)}(t) - M_x^{(j)}(t)\lambda_z^{(j)}(t) \qquad (14)$$

whereupon the gradients are added to the controls $v_x^{(j)}(t)$ and $v_y^{(j)}(t)$, whereby updated controls $v_x^{(j)}(t)$ and $v_y^{(j)}(t)$ are obtained, for which corresponding trajectories, costate vectors and gradients are calculated in the next iteration as well, wherein this iterative method is repeated until an arbitrarily defined abortion criterion is fulfilled. In the following, the method according to the present invention will be described in detail.

Before the gradients are added to the controls, the gradients can be multiplied with an arbitrary scaling factor (=step size) in the method according to the present invention. These step sizes can be constant and variable. Variable step sizes can be calculated in arbitrary ways, comprising conjugated gradients, quasi Newton methods like BFGS or limited-memory BFGS (L-BFGS), for example, as has been shown by Fouquieres et al. "Second Order Gradient Ascent Pulse Engineering", submitted to Magn. Reson. preprint: arXiv: 1102.4096).

Now we consider a set of N individual pulses $P^{(j)}$ having equal duration T (wherein the method is not restricted to pulses having equal duration) with rf amplitudes $v_x^{(j)}(t)$ and $v_y^{(j)}(t)$ and $j\in\{1, 2, \ldots, N\}$. For a given initial state $M^{(1)}(0)=M^{(2)}(0)= \ldots M^{(N)}(0)=M_i$, the corresponding N trajectories $M^{(j)}(t)$ of the magnetization vectors under the effect of the pulses $P^{(j)}$ can be calculated for $0\leq t \leq T$ using the Bloch equations. Without a restriction of generality, we simply assume that the quality factor $\Phi$ depends only on the final magnetization vectors $M^{(j)}(T)$. Then, the components of the costate vectors $\lambda^{(j)}(T)$ are given by $$\lambda_x^{(j)}(T) = \frac{\partial \Phi}{\partial M_x^{(j)}(T)}, \lambda_y^{(j)}(T) = \frac{\partial \Phi}{\partial M_y^{(j)}(T)}, \lambda_z^{(j)}(T) = \frac{\partial \Phi}{\partial M_z^{(j)}(T)} \qquad (15)$$

and the N trajectories $\lambda^{(j)}(T)$ can be calculated for $0\leq t \leq T$ by using the equation of motion of the costate vectors in analogy to Eq. (8). Skinner et al. describe (J. Magn. Reson, 163 (2003) 8-15), how the gradient of the quality factor $\Phi$ with respect to the controls $v_x^{(j)}(t)$ and $v_y^{(j)}(t)$ is given by the x and y components of the vectors $M^{(j)}(t)\times\lambda^{(j)}(t)$:

$$\frac{\delta\Phi}{\delta v_x^{(j)}(t)} = M_y^{(j)}(t)\lambda_z^{(j)}(t) - M_z^{(j)}(t)\lambda_y^{(j)}(t) \qquad (16)$$

$$\frac{\delta\Phi}{\delta v_y^{(j)}(t)} = M_z^{(j)}(t)\lambda_x^{(j)}(t) - M_x^{(j)}(t)\lambda_z^{(j)}(t) \qquad (17)$$

For example, consider the optimization of COOP excitation pulses with minimal overall phase error. If applied in successive scans, the real and imaginary parts of the accumulated signal $S_x+iS_y$ are proportional to the x and y components of the average magnetization vector $$\overline{M}(T) = \frac{1}{N}\sum_{j=1}^{N} M^{(j)}(T). \qquad (18)$$

The goal is to maximize $\overline{M}_x(T)$ and to minimize $\overline{M}_y(T)$ in order to minimize the phase error of the accumulated signal, while $\overline{M}_z(T)$ is irrelevant. This goal can be quantified by $$\Phi_e = 1 - (1-\overline{M}_x(T))^2 - a\overline{M}_y(T)^2, \qquad (19)$$

which is a generalization of the quality factor $\Phi_b$ (cf. Eq. (7)), where $M(T)$ is replaced by $\overline{M}(T)$, with $F=(1,0,0)^t$, $a_1=1$, $a_2=a$, and $a_3=0$. Here, the relative weight given to the deviations of $M_x$ and $M_y$ from the target values $F_x=1$ and $F_y=0$ can be adjusted by the parameter a. According to Eq. (15), the costate vectors are given by $$\lambda^{(j)}(T) = \frac{2}{N}(1 - \overline{M}_x(T), -a\overline{M}_y(T), 0)^t, \qquad (20)$$

which is independent of j, i.e. all costate vectors are identical at the end of the pulse ($\lambda^{(1)}(T)=\lambda^{(2)}(T)=\ldots=\lambda^{(3)}(T)$) and depend on the average magnetization vector $\overline{M}(T)$. However, the back propagation of the costate vectors according to the different pulses P(i) results in different trajectories $\lambda^{(j)}(t)$ for $0\leq t \leq T$.

With the trajectories $M^{(j)}(t)$ and $)\lambda^{(j)}(t)$, the gradients (16, 7) can be efficiently calculated, providing a powerful means for the simultaneous optimization of a set of mutually compensating COOP pulses. In the following section, illustrative examples will be given, to demonstrate the COOP approach. Experiments were performed on AV 250 and AV III 600 NMR spectrometers from Bruker wherein a sample of 1% $H_2O$ in $D_2O$ doped with copper sulfate ($CuSO_4$) was used.

In the following, the method according to the present invention is described exemplarily. As a first example, we consider the problem of completely eliminating all components of the average magnetization vector, i.e. $\overline{M}_x=\overline{M}_y=\overline{M}_z=0$ in the absence of $B_0$ gradients, $B_1$ inhomogeneity and relaxation effects, starting from z magnetization. Clearly, this cannot be accomplished by a single pulse and at least two scans are required to achieve this goal. We optimized groups of COOP pulses consisting of two or three individual pulses, using the quality factor $$\Phi_{elim}=1-\overline{M}_x(T)^2-\overline{M}_y(T)^2-\overline{M}_z(T)^2 \qquad (21).$$

DESCRIPTION OF THE PREFERRED EMBODIMENT

Figure 1:
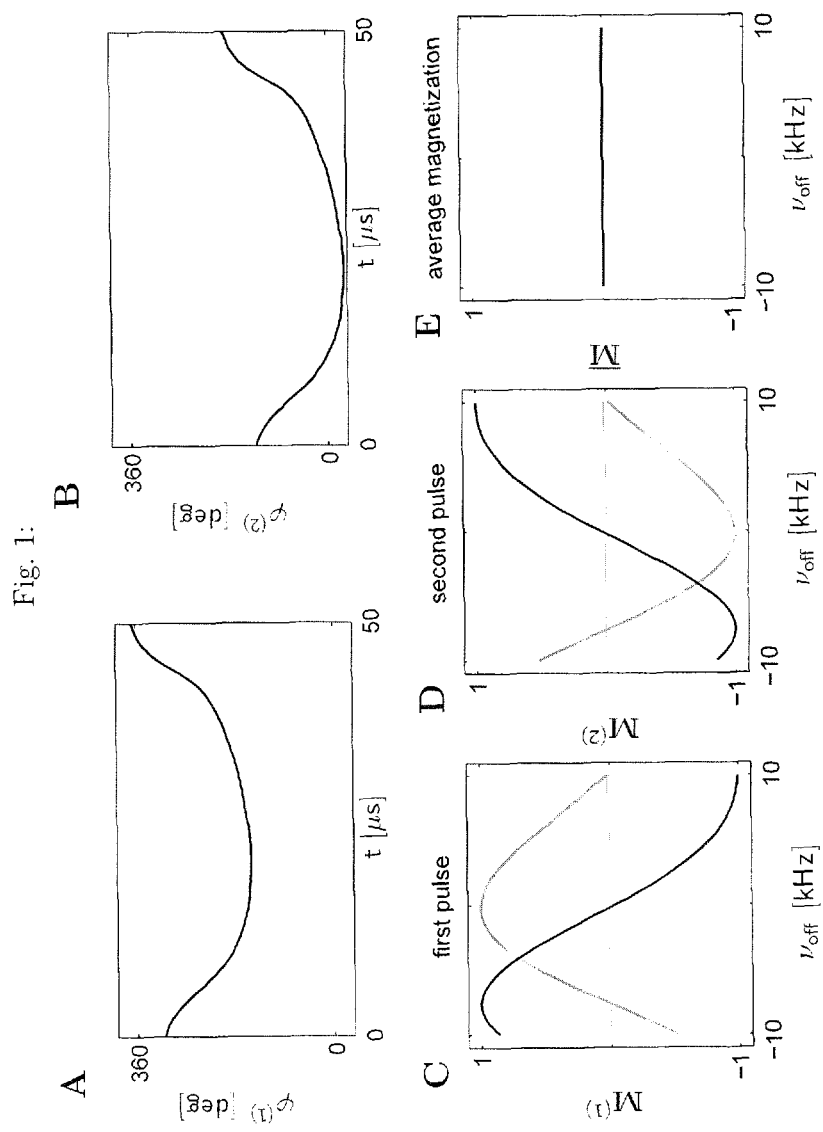
FIG. 1 shows optimized pulse shapes, final magnetization components after each individual pulse and components of the average final magnetization vector as a function of offset.

For the simplest case of a single spin on resonance, the extended GRAPE algorithm finds the intuitive solution of two rectangular 90° pulses with a relative phase shift of 180°. Similarly, the optimization of three COOP pulses yields three rectangular 90° pulses with phase differences of 120° and 240°, respectively, as expected (data not shown), demonstrating that the algorithm is able to rediscover simple phase cycles. If the elimination of magnetization is desired not only for the on-resonance case but for a finite range of offsets and limited rf amplitudes, the optimal solution is not clear a priori. For an offset range of ±10 kHz and a maximum rf amplitude of 10 kHz we optimized a group of two COOP pulses, consisting of two individual pulses with a duration of 50 µs each. For each individual pulse, a different random pulse shape was created at the start of the optimization, wherein no symmetry constraints were imposed, FIG. 1 shows the optimized pulse shapes, the final magnetization components after each individual pulse and the components of the average final magnetization vector as a function of offset. The two COOP pulses efficiently eliminate the average magnetization vector as expected. Here, the optimal solution consists of two saturation pulses that are identical up to an overall phase shift of 180°. Each individual saturation pulse brings the magnetization vector to the transverse plane and hence efficiently eliminates the z component in each scan with high fidelity for the desired range of offsets. The remaining transverse magnetization components are then averaged to zero by repeating the saturation pulse with a phase shift of 180°. This solution is not unexpected because a single saturation pulse could have been optimized and phase cycled, leading to the same result. However, initially it was by no means clear if this is in fact the best possible strategy. As the COOP approach is not limited to a restricted set of solutions (e.g. pairs of saturation pulses), it is also able to find unexpected solutions if they exist, as will be shown in the next examples.

FIG. 1 shows a group of two COOP pulses for the complete elimination of the average magnetization vector $\overline{M}$ for offsets in the range of ±10 kHz for a constant rf amplitude $v_{rf}$=10 kHz and a pulse duration of 50 µs. A and B show the phase modulations $\phi^{(1)}(t)$ and $\phi^{(2)}(t)$, simulated offset-profiles of $M^{(1)}(T)$, $M^{(2)}(T)$ and $\overline{M}(T)$ are shown in C, D and E. The x, y and z components are shown in black (x), dark gray (y) and bright gray (z), respectively.

Figure 2:
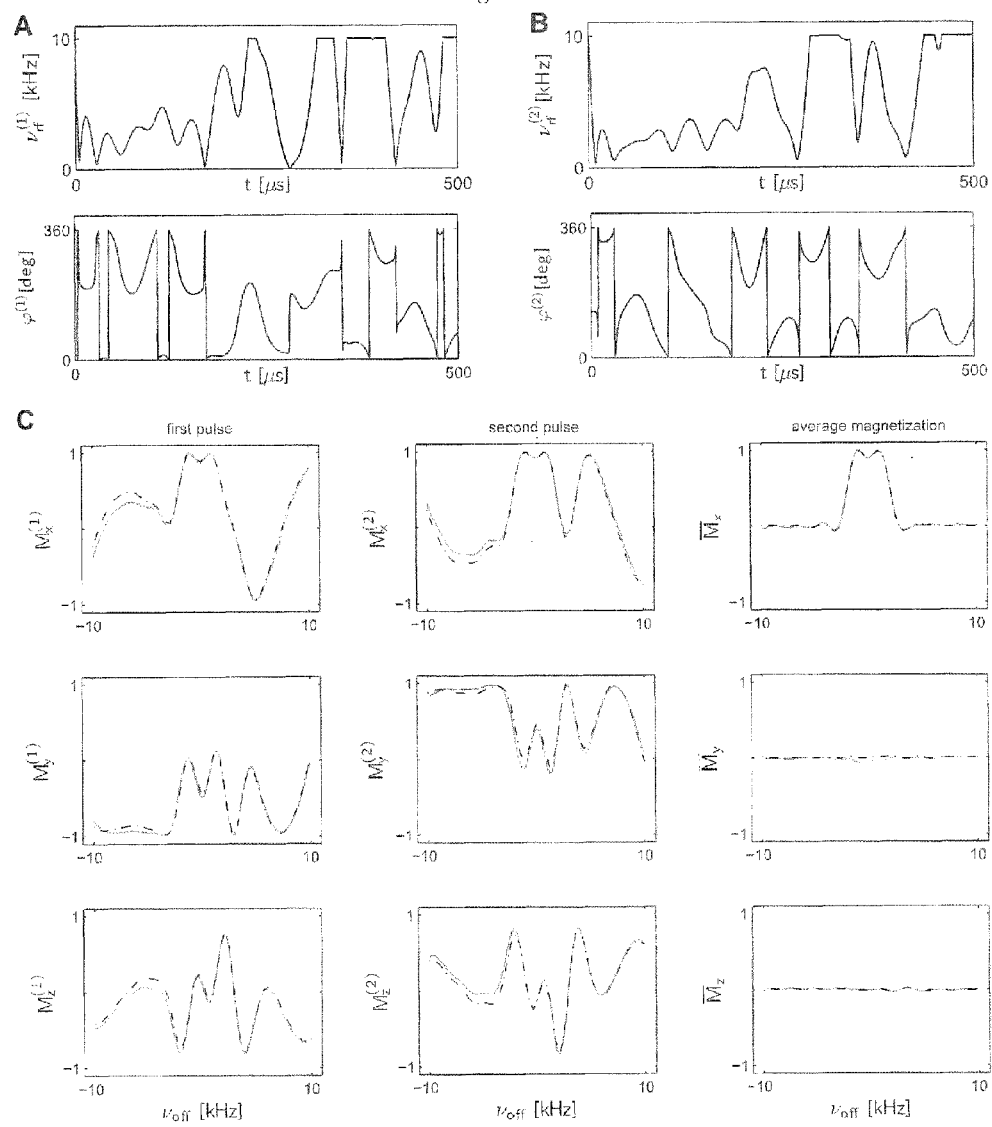
FIG. 2 shows simulated and experimental final magnetization components created by the individual pulses and the average magnetization vector.

As a second example, we consider band-selective COOP pulses that excite magnetization in a defined offset range and simultaneously eliminate the average magnetization vector in other offset ranges. We use the quality factor $\Phi_b$ (Eq. (7)) for various offset-dependent target states $F(v_{off})$. Here we consider the example where $F(v_{off})=(1,0,0)^t$ for $|v_{off}|\leq 2$ kHz (the "pass band") and $F(v_{off})=(0,0,0)^t$ for $2$ kHz$<|v_{off}|\leq 10$ kHz (the "stop band"). The pulse duration T and the maximum rf amplitude $v_{rf}^{max}$ were set to 500 µs and 10 kHz, respectively. In contrast to the first example, the COOP optimization yields two different pulses that are not simply related by an overall phase shift (FIG. 2). FIG. 2 also shows the simulated and experimental final magnetization components created by the individual pulses and the average magnetization vector. While the response of the individual COOP pulses appears to be erratic, the cancellation of the undesired terms is almost perfect. An excellent match is found between experimental (gray) and simulated (black) data.

Figure 3:
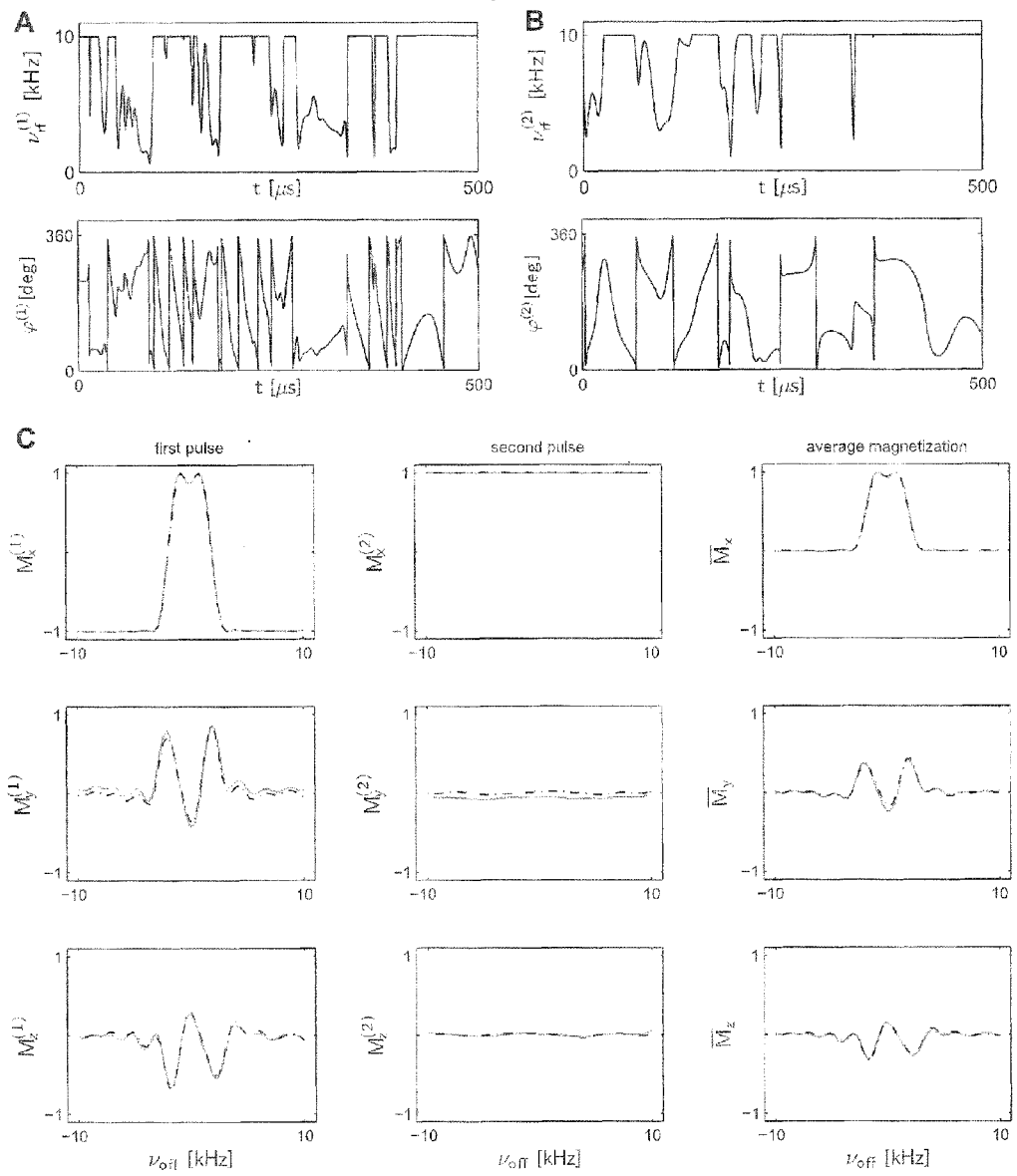
FIG. 3 shows the result of a conventional approach based on two individually optimized pulses.

For comparison, FIG. 3 shows the results of a conventional approach based on two individually optimized pulses: a broadband pulse with a target state $F_1(v_{off})=(1,0,0)^t$ for $|v_{off}|\leq 10$ kHz and a band-selective pulse with $F_2(v_{off})=(1,0,0)^t$ for $|v_{off}|\leq 2$ kHz and $F_2(v_{off})=(-1,0,0)^t$ for $2$ kHz$<|v_{off}|\leq 10$ kHz. These pulses also yield the desired average magnetization profile. Very good suppression of the x component is achieved by this approach in the stop band. However, large residual y and z components of the average magnetization vector of more than 40% remain in the vicinity of the transition regions at ±2 kHz (see FIG. 3). In contrast thereto, using the COOP approach, the undesired y and z components can be almost completely suppressed in the pass band, the stop band as well as in the transition region.

Similar results were found for band-selective inversion pulses and different ranges of pass and stop bands (data not shown). It is interesting to note that in the case of band-selective inversion (at simultaneous complete elimination of the average magnetization vector in the stop band), the COOP approach results in two very similar pulses with a relative phase shift of 180°. In this case, the target profile of the average magnetization vector can be approached by a pulse that inverts the magnetization in the pass band and brings it into the transverse plane in the stop band. By repeating the pulse with a phase shift of 180°, all transverse magnetization components are perfectly cancelled. Hence in this case, the COOP approach yields a solution that could also be constructed using a conventionally optimized single pulse combined with a phase cycle. However, it was by no means obvious before that this approach yields the optimal solution, which is obviously very different from the naive approach, namely combining individually optimized pulses for band-selective and broadband inversion.

FIG. 2 shows a group of two COOP pulses for band-selective excitation and saturation. The rf amplitudes $v_{rf}^{(j)}(t)$ and phases $\phi^{(j)}(t)$ for the two COOP pulses are shown in A and B. Simulated (black, dash-dotted curves) and experimental (gray, solid curves) components of $M^{(1)}(T)$, $M^{(2)}(T)$ and $\overline{M}(T)$ are shown in C.

FIG. 3 shows two conventional pulses that were independently optimized for band-selective and broadband excitation, respectively. The rf amplitudes $v_{rf}(t)$ and phases $\phi(t)$ for each individual pulse are shown in A and B. Simulated (black, dash-dotted curves) and experimental (gray, solid curves) components of $M^{(1)}(T)$, $M^{(2)}(T)$ and $\overline{M}(T)$ are shown in C.

Now we ask the question of whether the duration of broadband excitation pulses can be reduced using the COOP approach. In order to avoid phase errors in the resulting spectrum, a single pulse for broadband excitation of x magnetization is not allowed to create significant y components in the desired offset range. In contrast, the creation of relatively large y components $|M_y^{(j)}(T)|$ by the individual members of a cycle of COOP excitation pulses is acceptable, provided $|\overline{M}_y(T)|$ is small (and $\overline{M}_x(T)$ is large). This provides additional degrees of freedom in the optimization.

As a concrete example, we consider the optimal excitation of x magnetization with minimal phase errors in an offset range of ±20 kHz with a maximum rf amplitude of $v_{rf}^{max}=17.5$ kHz and a robustness with respect to variations of the rf amplitude of ±5%. For this problem, the duration of efficient optimal control based pulses could be reduced from 2 ms (described by Skinner et al. (J. Magn. Reson 163 (2003) 8-15)) to 500 μs (described by Skinner et al. (J. Magn. Reson 167 (2004) 68-74)) by generalizing the algorithm to take if limit limits into account during the optimization. Subsequently, the pulse duration could be reduced even further by Skinner et al. (J. Magn. Reson 172 (2005) 17-23) to only 125 μs by using a quality factor similar to $\Phi_c$ (Eq. (13)) for N=1 that is better adapted to the problem of excitation with minimal phase errors than quality factors based on $\Phi_a$ (Eq. (6)). For the same specifications, a single pulse (N=1) and groups of COOP pulses (N>1) were optimized using the quality factor $\Phi_c$ (Eq. (19)). The numerically determined quality factor $\Phi_c$ (Eq. (19)) with a=1 of the single 125 μs long pulse from (J. Magn. Reson 172 (2005) 17-23) is $\Phi_c=0.999852$. The gradient of the quality factor for the COOP pulse optimization can be efficiently approximated using the equations (10-11) to first order where $\lambda^{(j)}(T)$ is given by Eq. (14). For example, with a method according to the present invention, a comparable quality factor ($\Phi_c=0.999856$) can be achieved with a group of three COOP pulses with a reduced duration of only 100 μs of each individual pulse (see supplementary enclosures). Hence, in this case by using the method according to the present invention it is possible to reduce the duration of excitation pulses by an additional 20% without loss in pulse performance. The x component of the excited average magnetization vector is about 0.99, and the phase error is less than 0.4° for the entire offset range of 40 kHz.

Figure 4:
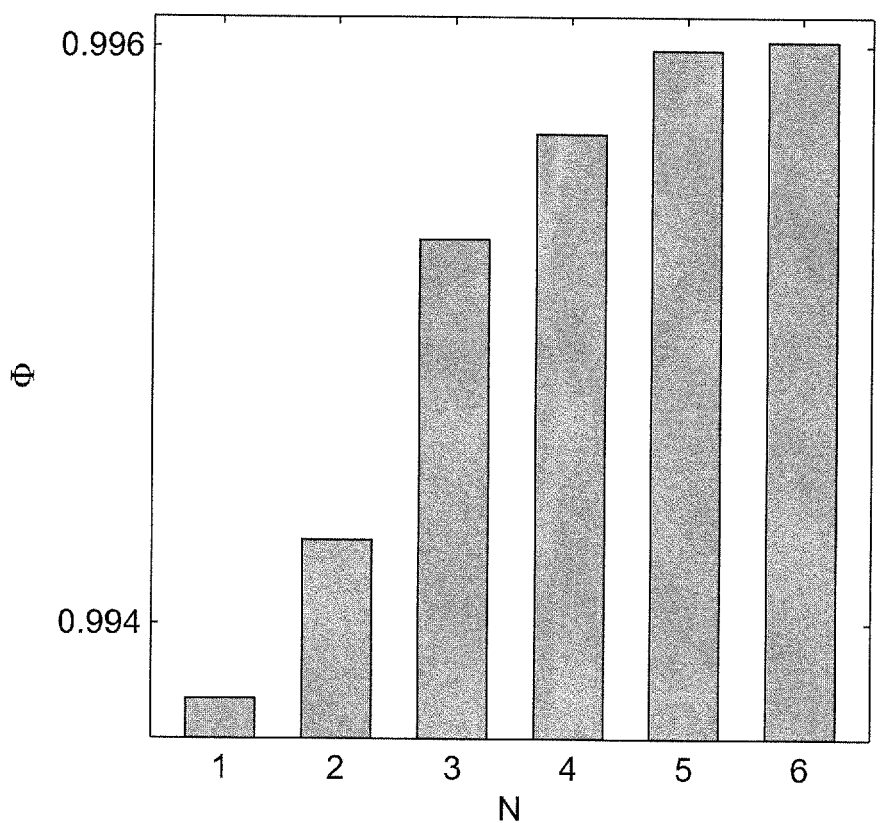
FIG. 4 shows achieved quality factors for a single pulse (N=1) and with COOP pulses with N from 2 to 6.
Figure 5:
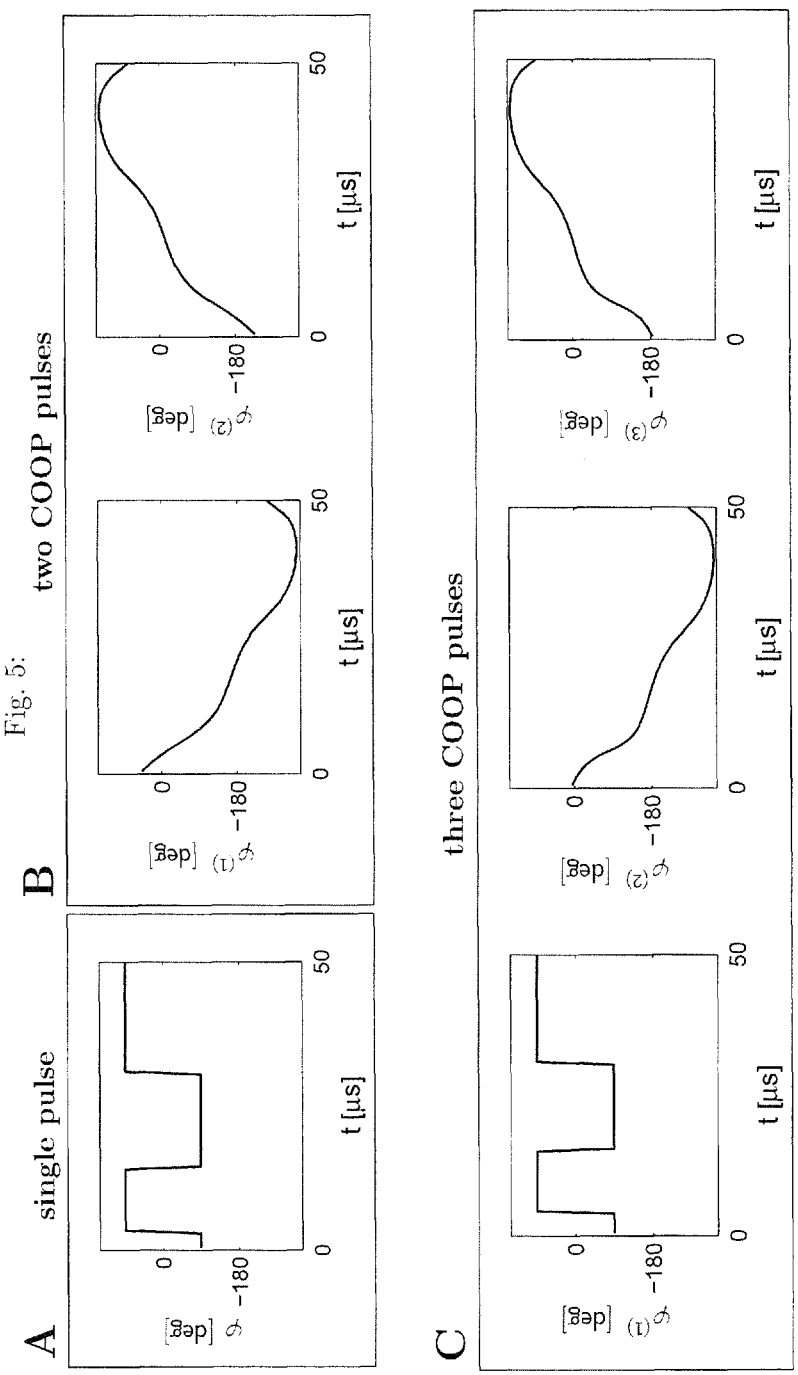
FIG. 5 shows the optimized pulses for N=1, 2 and 3.

In order to explore the performance limit of even shorter pulses, we also optimized single and COOP pulses with a duration of T=50 μs, which is only 3.5 times longer than the duration of a hard 90° pulse for an rf amplitude of 17.5 kHz. FIG. 4 shows the achieved quality factors for a single pulse (N=1) and for COOP pulses with N from 2 and 6. The optimized pulses for N=1, 2, and 3 are shown in FIG. 5. All pulses have constant amplitude, taking full advantage of the maximum allowed rf amplitude of $v_{rf}^{max}=17.5$ kHz. The optimal single pulse (N=1) shown in FIG. 5A and is purely phase-alternating with phases ±λ/2. Levitt has found (Prog. Nucl. Magn. Reson. Spectrosc. 18 (1986) 61-122) that this class of phase-alternating pulses implies the following symmetry relations for the x and y components of the excited magnetization vectors at offsets ±v:

$$M_x(v)=M_x(-v) \quad (22)$$

$$M_y(v)=M_y(-v) \quad (23)$$

(In addition, $M_z(v)=M_z(-v)$, however this relation is not relevant here, as $\Phi_c$ has no explicit $M_z$ dependence, cf. Eq. (13).) The symmetry relations for the x and the y components of the final magnetization vectors match the symmetry of the problem. Maximum $M_x(v)$ is desired both for positive offsets (between 0 and 20 kHz) and for negative offsets (between 0 and -20 kHz), and, according to Eq. (22), a large value for $M_x(v)$ implies an equally large value for $M_x(-v)$. In addition, $|M_y|(v) \approx 0$ is desired both for positive and negative offsets, and, according to Eq. (23), a small $|M_y(v)|$ at frequency v implies an equally small $|M_y(-v)|$.

In contrast to the case N=1, the COOP pulses for N=2 shown in FIG. 5B are not phase-alternating but have smooth phase modulations. However, the phase modulations are not independent but are related by phase inversion and an additional phase shift by)) π:

$$\phi^{(2)}(t)=-\phi^{(1)}(t)+\pi \quad (24)$$

corresponding to a reflection of the phase around a/2. (In terms of the x and y components of the rf amplitudes, this relation corresponds to $v_x^{(2)}=-v_x^{(1)}$ and $v_y^{(2)}=v_y^{(1)}$.) Applying well known principles of pulse sequence analysis, e.g. as shown by Levitt (Prog. Nucl. Magn. Reson. Spectrosc. 18 (1986) 61-122), it is straightforward to show that Eq. (24) implies the following symmetry relations between the transverse components of the excited magnetization vectors after the first and second pulse:

$$M_x^{(2)}(v)=M_x^{(1)}(-v) \quad (25)$$

$$M_y^{(2)}(v)=-M_y^{(1)}(-v) \quad (6)$$

(and in addition $M_z^{(2)}(v)=-M_z^{(1)}(-v)$.). As a direct consequence of Eqs. (25) and (26), the transverse components of the average magnetization vector after the COOP pulse pair are related by:

$$\overline{M}_x(v)=\overline{M}_x(-v) \quad (27)$$

$$\overline{M}_y(v)=-\overline{M}_y(-v) \quad (28)$$

Figure 6:
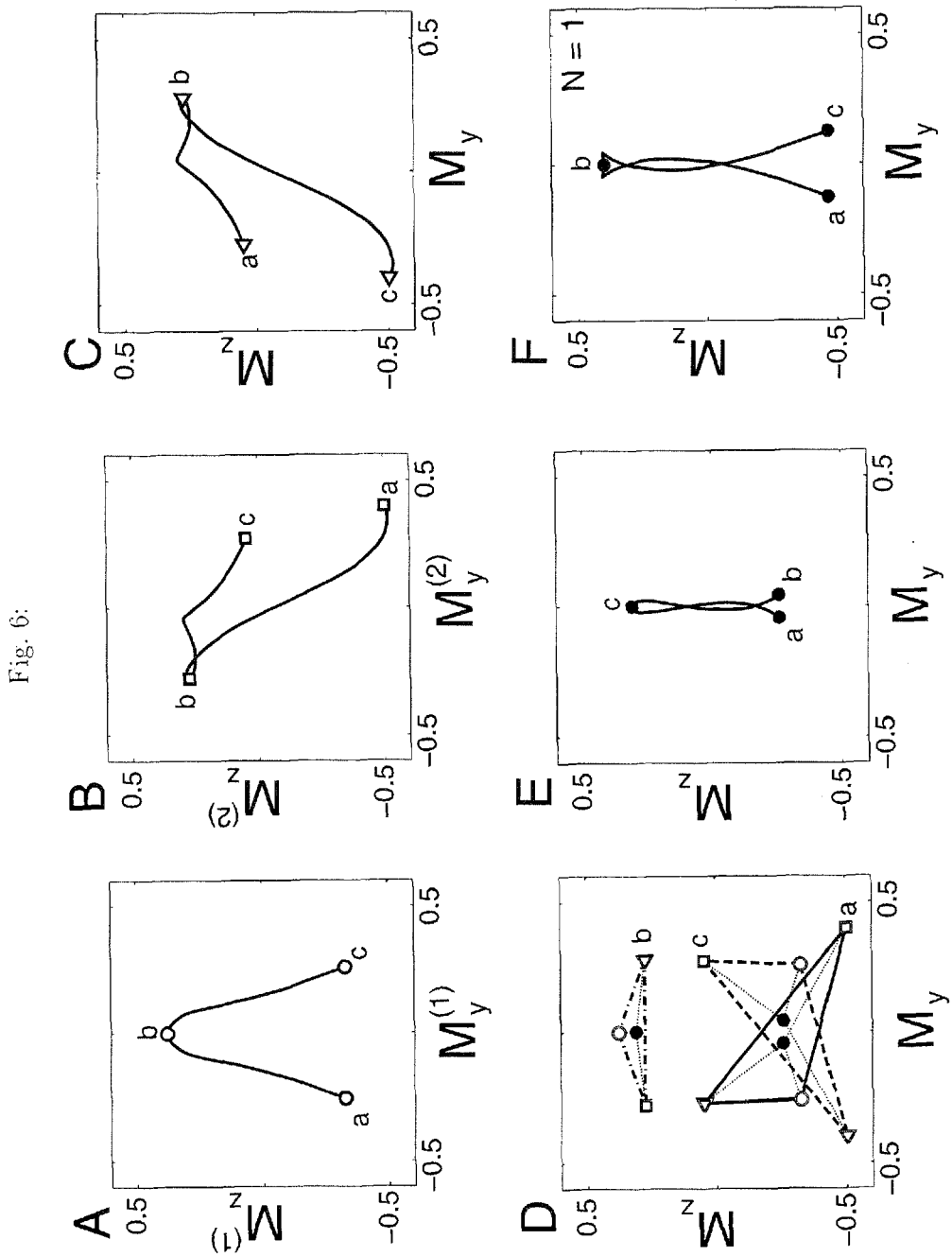
FIG. 6 shows the location of the individual and of the average magnetization vectors in the y-z plane after the COOP pulses.

This is analogous to the relations in the equations (22) and (23) for a single phase-alternating pulse and which matches the symmetry of the problem as discussed above. The symmetry relations for the average transverse magnetization components (equations (27) and (28)) can always be realized if the group of N COOP pulses consists of symmetry-related pulse pairs (with phase relations corresponding to Eq. (24)) and/or phase-alternating pulses with phases ±π/2. For example, for N=3 the group of COOP pulses consists of one symmetry-related pulse pair and one phase-alternating pulse (cf. FIG. 5C). For N=4, 5, and 6, we always find two symmetry-related pulse pairs and an according number of phase-alternating pulses. FIG. 6 shows the location of the individual and of the average magnetization vectors in the y-z plane after the COOP pulses for (N=3) (cf. FIG. 5C). The points denoted a, b, and c correspond to offsets of -20 kHz, 0 kHz and 20 kHz, respectively. The FIGS. 6 B and C illustrate the symmetry relations of equations (22,23) (27, 28). Relatively large y components of up to 40% are found for each individual pulse, illustrating the additional degrees of freedom gained by the COOP approach. However, the average magnetization vectors are located very close to the x-z plane as shown in FIG. 6 E. In FIG. 6 F, the corners of the triangles represent the locations of the magnetization vectors after the individual pulses and the centers of the triangles indicate the location of the average magnetization vectors for offsets -20 kHz (a), 0 kHz (b) and 20 kHz (c), illustrating the averaging process. For comparison, FIG. 6 D also displays the location of the magnetization after the optimized single pulses (cf. FIG. 5 A).

Figure 7:
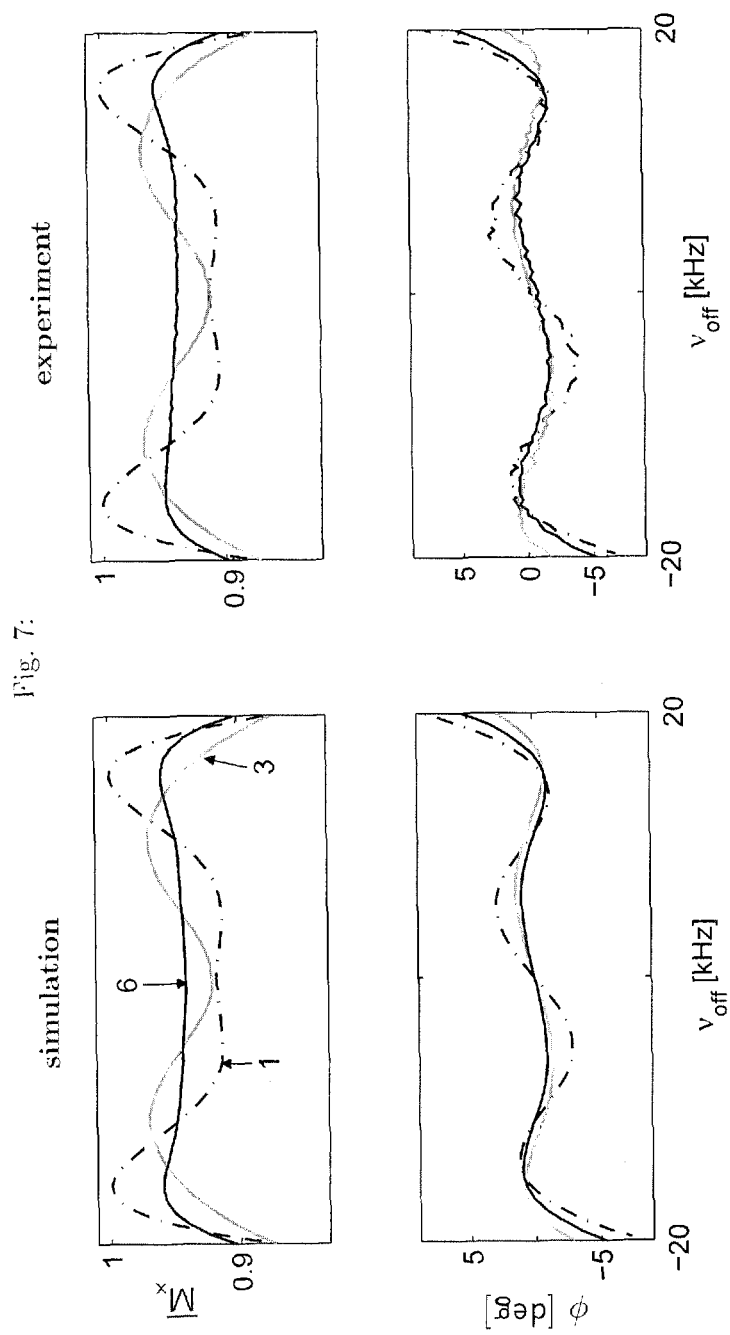
FIG. 7 compares the simulated and experimental COOP pulses.

A good match is found between the simulated and experimental performance of the COOP pulses, as demonstrated in FIG. 7, where the x components and the phases of the average magnetization vector is shown for the optimized single pulse and for the COOP pulses with N=3 and N=6. For the single pulse, the excitation efficiency is below 92% for a large range of offsets, whereas for N=6, the excitation efficiency reaches 95% for almost the entire offset range. At the same time, the largest phase error is reduced from about 8° to 5° at extreme offsets and from about 3° to less than 1.3° for offsets between ±18 kHz.

In (J. Magn. Reson. 172 (2005) 17-23), Skinner et al. conjectured that for a single pulse a duration of 100 μs is a conservative lower limit for achieving better than 95% excitation efficiency and a phase error of no more than 4° in a relative bandwidth of $\Delta v_{off}/v_{rf}^{max}=2.3$ and with rf tolerance of ±5%. With the COOP method according to the present invention, we are able to push the lower limit on pulse length below 65 μs for N=6 (data not shown). FIG. 4 shows the quality factor $\Phi$ for excitation of x magnetization with pulse durations of T=50 µs as function of the number of COOP pulses N.

FIG. 5 shows excitation pulses with minimized phase errors with a duration of T=50 µs: (A) conventional single pulse, (B) group of two COOP pulses with N=2, (C) group of three COOP pulses with N=3. For both pulse pairs with "smooth" phase modulation in B and C, the individual pulses are symmetry-related by $\phi^{(j+1)}(t)=\phi^{(j)}(t)-\pi$, which is equivalent to Eq. (24).

In A-C, FIG. 6 shows the individual offset-profiles of the group of three COOP pulses (N=3) from FIG. 5. The final states of $M_y^{(j)}(T)$ and $M_z^{(j)}(T)$ within an offset frequency range of ±20 kHz are displayed, where in each of the figures, the offsets −20 kHz, 0 kHz and 20 kHz are indicated by symbols (open circles, squares and triangles). For these three offsets, the y and z components of $M^{(1)}(T)$, $M^{(2)}(T)$ and $M^{(3)}(T)$ (open symbols) and of $\overline{M}(T)$ (solid discs) are shown in D, illustrating the cancellation of phase errors. Figure E shows the location of the average magnetization vector $\overline{M}(T)$ for the entire offset range of ±20 kHz. For comparison, the location of the magnetization vector M(T) for the single, conventionally optimized pulse (N=1, cf. FIG. 5 A) is shown in F.

In FIG. 7, simulated and experimental offset-profiles for the average magnetization $\overline{M}_x(T)$ and the phase error $\phi(T)$ for a single pulse (N=1, cf. FIG. 5 A) and groups of COOP pulses with N=3 (cf. FIG. 5 C) and N=6 are shown.

Figure 8:
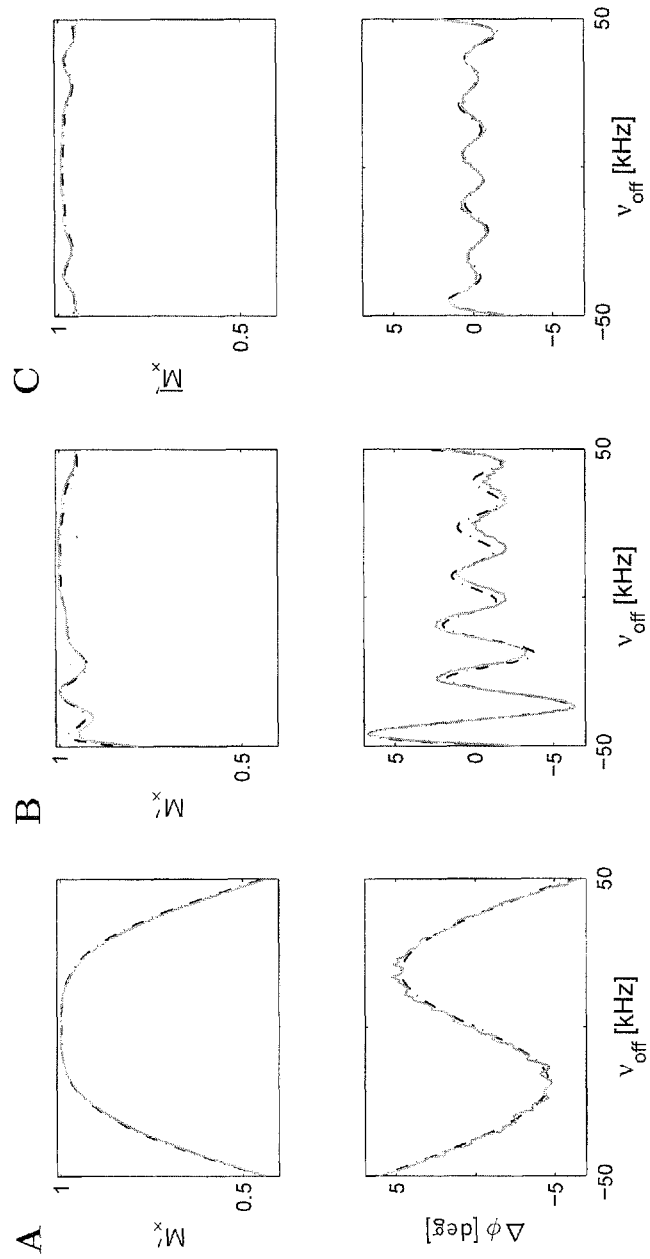
FIG. 8 shows the offset profile of the x component of the $\overline{M}_x(T)$ magnetization and the residual phase error.

In the previous section the target was to create pulses with offset-independent phase, i.e. pulses where no phase correction of first or higher order is necessary. As Gershenzon et al. show in (J. Magn. Reson. 192 (2008) 335-343), an even larger bandwidth can be achieved for so-called ICEBERG pulses (Inherent Coherence Evolution optimized Broadband Excitation Resulting in constant phase Gradients) that create transverse magnetization with a linear offset dependence. For example, for a simple rectangular 90° pulse, the resulting phase is almost linear for a large range of offsets and can be corrected by first-order phase correction. FIG. 8 shows the offset profile of the x component of the $\overline{M}_x(T)$ magnetization and the residual phase error after first-order phase correction with 2.9°/kHz for a rectangular 14.29 µs 90° pulse, corresponding to an rf amplitude of $v_{rf}$=17.5 kHz. Over a range of ±50 kHz, the phase error is less than about 5°. However, for offset frequencies beyond ±30 kHz the excitation efficiency decreases rapidly.

A single pulse and a group of two COOP pulses (N=2) with a duration of 60 µs each, a maximum rf amplitude 17.5 kHz, 5% rf inhomogeneity for a bandwidth of ±50 kHz allowing for the same first-order phase correction of 2.9°/kHz as for the simple rectangular pulse were optimized. Simulated and experimental results are displayed in FIG. 8. The performance of the optimized single with larger transverse magnetization of more than 90% pulse (except for offsets near −50 kHz where the efficiency drops to about 80%) lies significantly above the performance of the simple rectangular pulse with 45% and comparable phase errors. However, the performance of the optimized COOP pulses shows a significant further improvement with an excitation efficiency of more than 95% and phase errors of less than 2.4° over the entire offset range of ±50 kHz.

Figure 9:
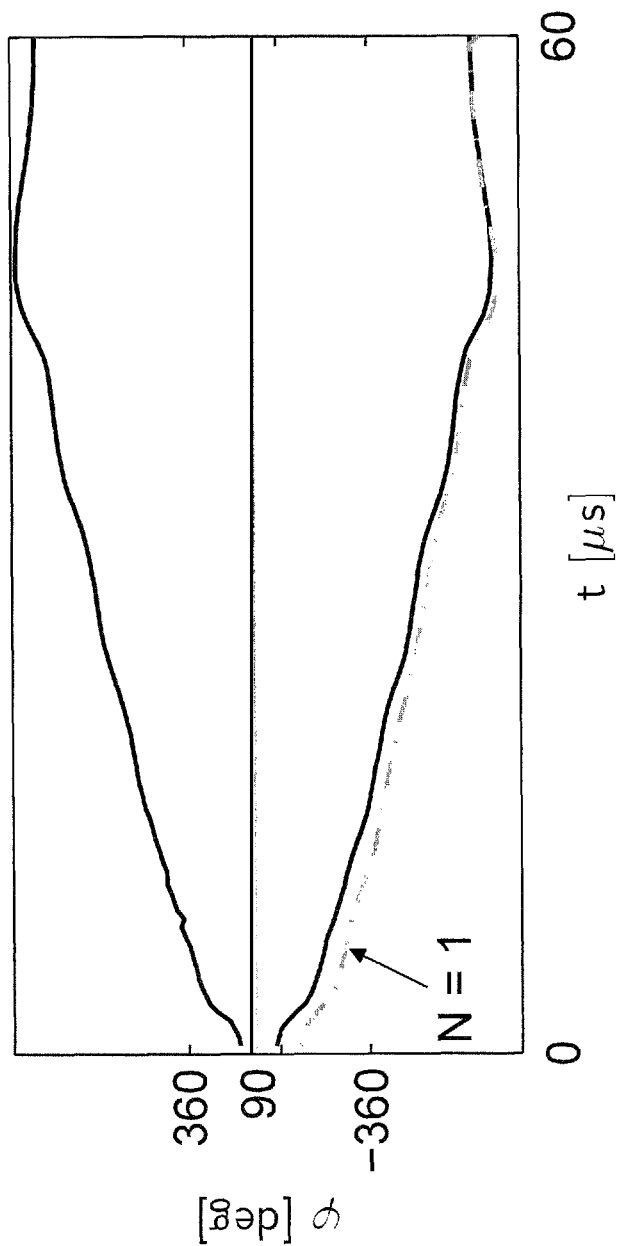
FIG. 9 shows a single ICEBERG and a group of COOP ICEBERG pulses.

FIG. 8 shows offset profiles for $\overline{M}'_x(T)$ and the phase deviation $\Delta\phi$ for a single rectangular pulse (A), an optimized individual ICEBERG pulse with N=1 (B, cf. dash-dotted curve in FIG. 9) and a group of COOP pulses with N=2 (C, cf. solid curves in FIG. 9). $\overline{M}'_x(T)$ is the x-component of $\overline{M}(T)$ and $\Delta\phi$ is the residual phase error after a first-order phase correction of 2.9°/kHz. Solid gray and dash-dotted black curves represent experimental and simulated data.

FIG. 9 A single (dashed-dotted gray curves) ICEBERG and a group of COOP ICEBERG pulses (solid black curves, N=2). For the COOP pulse pair the symmetry relation from Eq. (24) is approximately fulfilled.

A further example demonstrating the power of the COOP approach according to the present invention is motivated by the WET (water suppression enhanced through $T_1$ effects) solvent suppression sequence of Ogg et al, (J. Magn. Reson. B 104 (1994) 1-10). In order to also suppress solvent signals in regions away from the center of the rf coil and therefore experiencing smaller rf amplitudes, pulses are required that act as broadband 90° pulses for the full rf amplitude but that do not excite the solvent signal in regions of the sample where the rf amplitude is significantly scaled down. Zhang et al. (J. Magn. Reson 143 (2000) 382-386) and Bax (J. Magn. Reson 64 (1985) 142-145) show that one solution is based on composite pulses, such as the $90°_x 90°_y 90°_{-x} 90°_{-y}$ pulse, which is applied in every scan. However, by Zhang et al. (J. Magn. Reson 143 (2000) 382-386) in multi-scan experiments, improved performance was found if in three out of four scans a simple rectangular $90°_x$ pulse is used and in one out of four scans a simple rectangular $270°_{-x}$ pulse. This group of four pulses ($90°_x$, $90°_x$, $90°_x$, $270°_{-x}$), which are applied in successive scans, was derived in J. Magn. Reson 13 (2000) 382-386 based on linear response theory, which however is strictly valid only for flip angles approaching zero. In contrast, the COOP approach according to the present invention which is disclosed herein allows to develop groups of COOP pulses optimized for this task, taking into account the full non-linear spin dynamics.

To illustrate this, we optimized COOP pulses according to the method shown by Kobzar et al. in (J. Magn. Reson. 173 (2005) 229-235) with an excitation pattern as a function of offsets $v_{off}$ and rf scaling factor s that is adapted to the problem (see FIG. 10). For rf scaling factors in the range 0.95≤s≤1.05, the goal is to excite x magnetization in an offset range of ±5 kHz with minimal phase error. For rf scaling factors in the range 0≤s≤0.6, the goal is to minimize the transverse component $\overline{M}_\perp=(\overline{M}_x^2+\overline{M}_y^2)^{1/2}$ of the average magnetization vector for a reduced range of offset (near the solvent resonance) of ±500 Hz. We assume initial z magnetization and a maximum nominal rf amplitude of $v_{rf}^{max}$=20 kHz.

Figure 10:
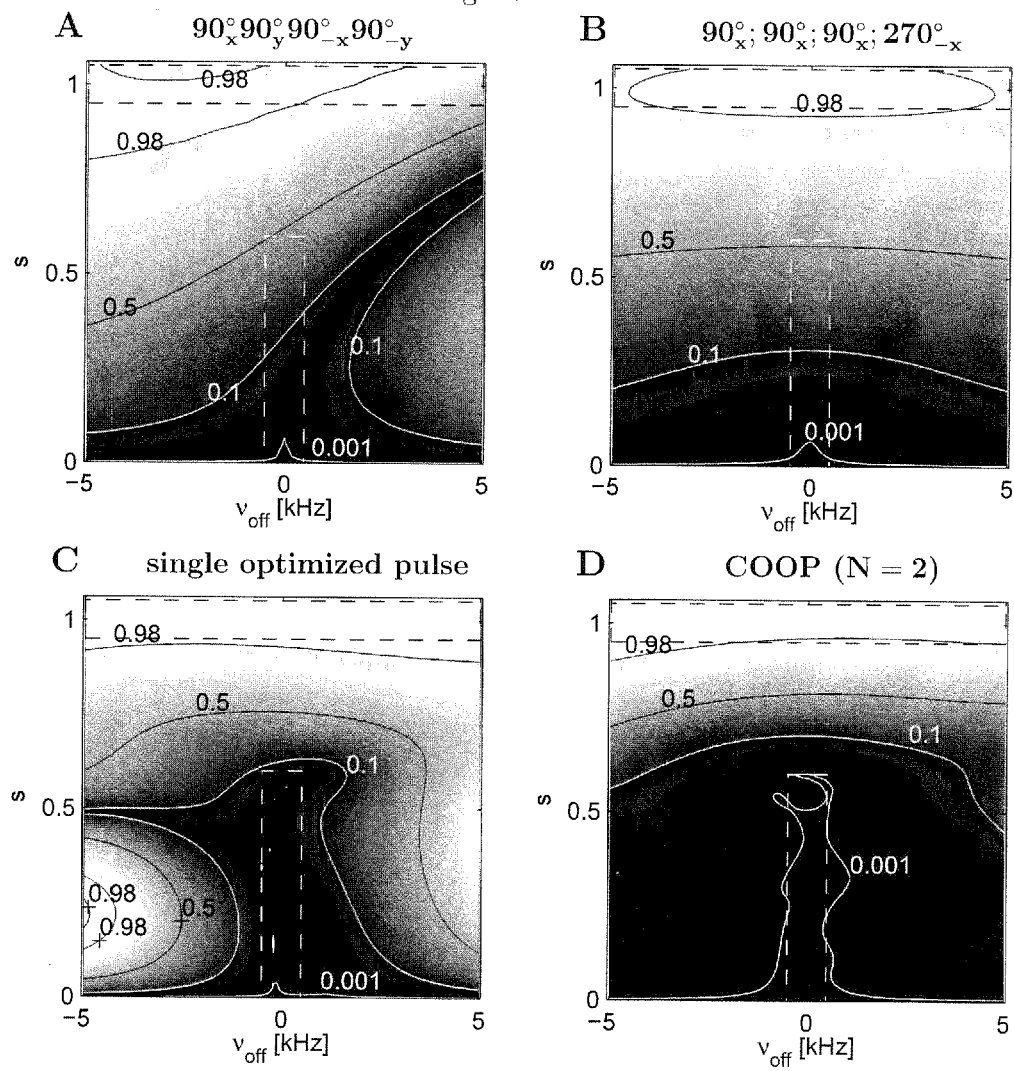
FIGS. 10 and 11 show the performance of an optimized group of two COOP pulses for each of four individual COOP pulses.
Figure 11:
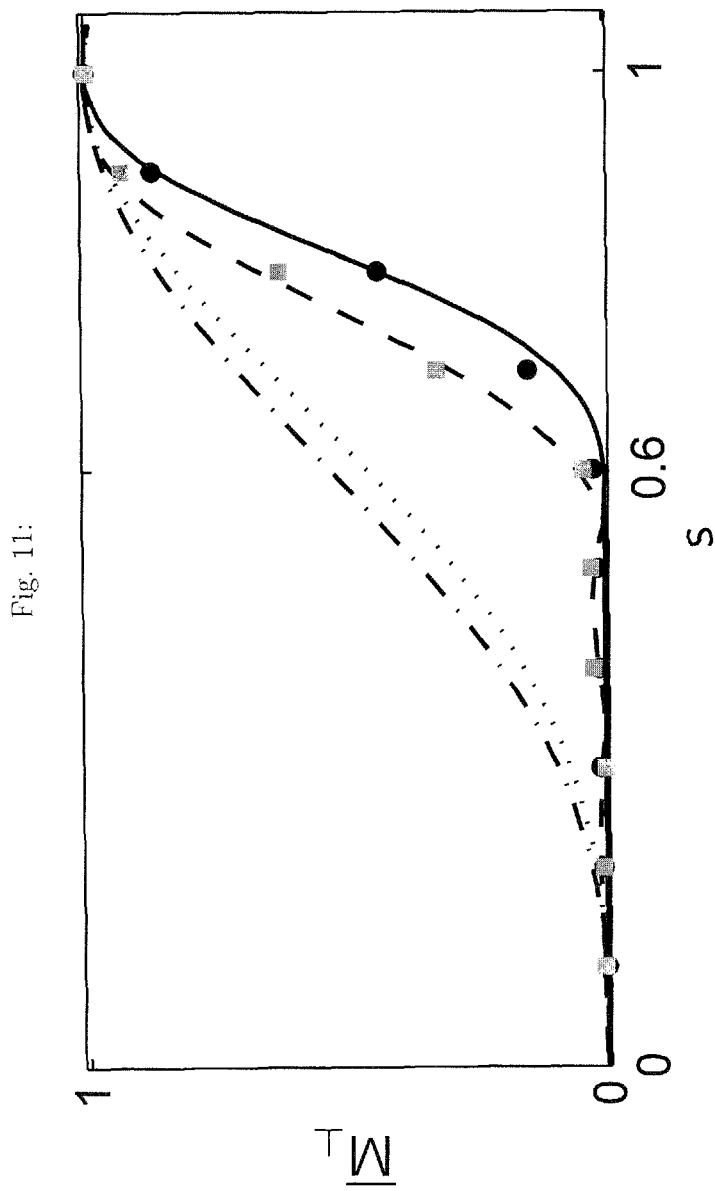

The FIGS. 10 and 11 show the performance of an optimized group of two COOP pulses (N=2) with a duration T=200 µs for each of the four individual COOP pulses. For comparison, we also show the performance of the composite pulse $90°_x 90°_y 90°_{-x} 90°_{-y}$ from J. Magn. Reson 64 (1985) 142-145, of a sequence based on ($90°_x$, $90°_x$, $90°_x$, $270°_{-x}$) (from J. Magn. Reson 143 (2000) 382-386), and an optimized individual pulse (N=1).

FIG. 10 shows a comparison of the average transverse magnetization as a function of offset $v_{off}$ and rf scaling s for a group of COOP WET pulses (D, N=2) with the $90°_x 90°_y 90°_{-x} 90°_{-y}$ composite pulse from J. Magn. Reson. 64 (1985) 142-145 (A), the four-scan sequence based on $90°_x$; $90°_x$; $90°_x$; $270°_{-x}$ (B, J. Magn. Reson 143 (2000) 382-386) and an optimized individual pulse (C, N=1). The areas for which optimal excitation and optimal suppression of transverse magnetization are desired are indicated by black and white, dashed rectangles.

FIG. 11 shows slices from FIG. 10 A (dotted), B (dash-dotted), C (dashed) and D (solid curve) for the on-resonance case. The gray squares and black discs represent experimental data for the pulse optimized according to the state of the art from FIG. 10 C and the COOP WET pulse according to the present invention from FIG. 10 D, respectively.

A further example that shows the advantages of the present invention with respect to the state of the art, are heteronuclear and homonuclear decoupling. The following example shows the advantages of the invention by means of heteronuclear decoupling, without being restricted thereto. The present invention can also be used to develop homonuclear decoupling pulses. Heteronuclear decoupling means suppression of the heteronuclear coupling evolution. Ernst et al. show (Principles of nuclear magnetic resonance spectroscopy in one and two dimensions. Clarendon Press, 1987) that simplified NMR spectra that are easier to interpret than spectra having been recorded without decoupling, and that additionally show an improved signal to noise ratio due to the increased intensity of decoupled signals, can be obtained by heteronuclear decoupling. The decoupling sequences according to the state of the art result in undesired signal contributions. Undesired signal contributions in the context of decoupling comprise decoupling side bands as well as deviations from a desired offset profile. For instance, a desired offset profile is a constant and maximum signal amplitude of the observed spin, which is independent from the resonance offset of the decoupled spin, the frequency of which the decoupling sequence is irradiated at. Further desired offset profiles comprise band selective decoupling, as it has been demonstrated by Eggenberger et al. in J. Magn Reson 100 (1992) 604-610 and by Zuiderweg et al. in J. Magn. Rosen. 93 (1991) 653-658, or a defined scaling of the coupling, as it has been demonstrated by Riek et al. in J. Am. Chem. Soc. 125 (2003) 16104-16113. A constant and maximum signal amplitude as a desired offset profile is particularly of relevance with regard to decoupling sequences which are to be of applied in quantitative NMR spectroscopy.

One method for the reduction of decoupling sidebands is the so called DESIRE method which has been shown by Kupce in the U.S. Pat. No. 688,348 and by Kupce et al. in J. Magn. Reson. 151 (2001) 142-145. DESIRE is a 2D NMR method wherein in the direct frequency dimension F2, the spectrum is resolved with respect to the chemical shift, as it is the case for a conventional excitation experiment. In the indirect dimension F1, the spectrum is resolved with respect to the frequency splitting of the decoupling sidebands, relative to the respective main signal. That is, the excitation spectrum corresponds to the slice of the 2D spectrum at F1=0, signals of the decoupling sidebands appear at F1≠0. A spectrum with an about 100-fold reduced intensity of the side bands can be obtained by this method. However, in order to obtain sufficient resolution in F1, numerous experiments with different $t_1$-evolution times are necessary. (In J. Magn. Reson 151 (2001) 142-146, Kupce et al. show spectra wherein 64 and 128 corresponding experiments were carried out, respectively.) A disadvantage of this method is that although sidebands are reduced by using DESIRE, this is however not the case for the deviations from a desired excitation/decoupling profile. In addition, the possibility, that the undesired signal contributions created by the decoupling pulses of the different scans may cancel, is not used.

In J. Magn. Reson. 122 (1996) 81-8, Kupce et al demonstrate a method for the reduction of decoupling sidebands, wherein the undesired signal contributions created by the decoupling pulses of the different scans may cancel. Therein, in a first scan, decoupling is carried out with low power exclusively ("low-level decoupling"). In all subsequent scans, first, decoupling is carried out with high power ("high-level decoupling"), followed by decoupling with low power ("low-level decoupling"). Therein, the duration of high power decoupling is increased stepwise with each following scan. Thus it is possible to partly cancel the undesired signal contributions created by the decoupling pulses of the different scans. A further development of this method for polymer analytics was presented by Zhou et al. in J. Magn. Reson. 187 (2007) 225-233. A significant reduction of the decoupling sidebands is possible by using the bilevel decoupling method. Disadvantages of this method are the high rf intensities during high power decoupling and the lacking suppression of deviations of a desired offset profile. The GRAPE-tracking method shown by Neves et al in J. Magn. Reson. 201 (2009) 7-17 makes it possible to numerically optimize non-periodic decoupling sequences for a single scan. Using the GRAPE-tracking method, broadbanded decoupling pulses for in vivo applications, that need a low rf intensity, could be optimized. The obtained results substantially exceed the quality of existing methods. The possibility to cancel undesired signal contributions by averaging several scans has not been used so far.

As was shown by Akoka et al in J. Magn. Reson. 185 (2007) 50-58, conventional decoupling pulse sequences create too large deviations from a desired offset profile so that they cannot be used in quantitative NMR. An advantageous desired offset profile for quantitative NMR is a constant and maximum signal amplitude. Akoka et al. show in the same place how these deviations being undesired system states can be reduced by using special adiabatic decoupling sequences. However, this approach does not make use of the possibility to use different pulses in several scans and, in addition, it is restricted to decoupling sequences that comprise sequences of adiabatic inversion pulses. Moreover, high rf amplitudes are necessary for the decoupling sequences shown by Akoka et al. in J. Magn. Reson. 185 (2007) 50-58.

The COOP method of the present invention makes it possible to simultaneously optimize decoupling pulses that cancel each other's errors. Thus, both undesired signal contributions, such as, for example, decoupling sidebands and/or deviations from a desired offset profile can be eliminated. An exemplary quality factor for the optimization of COOP decoupling pulses is $$\Phi_{decoupling} = \frac{1}{N_\epsilon N_\nu} \sum_{p=1}^{N_\epsilon} \sum_{q=1}^{N_\nu} \phi \qquad (29)$$

wherein $N_\epsilon$ corresponds to the number of considered rf scaling factors s, $N_\nu$ corresponds to the number of considered offset frequencies $\nu_{off}$. Therein, the COOP decoupling sequence is divided into $N_{acq}$ acquisition points. A possible quantification for the quality of the COOP decoupling sequence according to the present invention at the k-th acquisition point for N COOP pulses depends on the expectation value for $I_z$:

$$\bar{s}_k = \overline{\langle I_x \rangle} = \frac{1}{N} \sum_{j=1}^{N} \langle I_x^{(j)} \rangle. \qquad (30)$$

It is advantageous for the method according to the invention to use $$1 - a(1-\bar{s}_k)^n \qquad (31)$$

as a measure for the quality of the COOP decoupling sequence at the k-th acquisition point for N COOP pulses, wherein n is an even integer, preferably n=2 and wherein a is a real, positive scaling factor.

Thus we can write for φ in Equation 29:

$$\phi = \frac{1}{N_{acq}+1} \sum_{k=0}^{l} (1 - (1-\bar{s}_k)^n) \exp\{-\kappa T_k\} \qquad (32)$$

Therein, relaxation effects are taken into account by the term exp{-κT_k}, as it has been demonstrated by Neves et al. in J. Magn. Reson. 201 (2009) 7-17. Thus, in this example we obtain for the costate of the j-th COOP decoupling pulse at the time of the k-th acquisition point $T_k$ $$\lambda_k^{(j)}(T_k) = \frac{\partial \phi}{\partial I_x^{(j)}(T_k)} = \frac{n}{N_{acq}+1}(1+\bar{s}_k)\exp\{-\kappa T_k\}I_x \qquad (33)$$

In analogy to the above examples, at the acquisition point $T_k$, $\lambda_k^{(j)}(T_k)$ is identical for all COOP pulses, however it is back-propagated individually according to the j-th COOP decoupling pulse. In contrast to the preceding examples, here, the quality φ is not only dependent on the N final system states at the end of the N COOP pulses, but also on the system states at times $T_k$ of all $N_{acq}$ acquisition points of all N COOP pulses.

According to the present example, the gradient of the quality function Φ for the l-th pulse increment of the j-th COOP pulse is $$\frac{\delta \Phi}{\delta u_\alpha^{(j)}(l)} = \frac{1}{N_\epsilon N_\nu} \sum_{p=1}^{N_\epsilon} \sum_{q=1}^{N_\nu} \frac{\delta \phi(\epsilon^{(p)}, \nu_{off}^{(q)})}{\delta u_\alpha^{(j)}(l)} \qquad (34)$$

wherein ε is the rf scaling factor and α=x or α=y or α=z, wherein in the present example α=x or α=x are possible. In addition, in the present example, the following holds true $$\frac{\delta \Phi}{\delta u_\alpha^{(j)}(l)} = -2i\pi\epsilon\Delta t \sum_{k>m} \lambda_k^{(j)}(t_l)[I_\alpha, \rho_l^{(j)}] \qquad (35)$$

wherein m=⌊l/M⌋ and M is the number of pulse increments in-between two acquisition points and $t_l$ is the point in time at which the l-th pulse increment is applied. In this example, the duration of a pulse increment is chosen to be constant and takes the value Δt, wherein the method according to the present invention is not restricted to constant values for Δt.

So far, we have only regarded examples, in which COOP pulses are applied in several scans at the same position of a pulse sequence, generalizing and complementing the concept of phase cycling. Now we draw our attention to an embodiment of the present invention, wherein COOP pulses are applied in a single scan and at different positions of a pulse sequence. However, the present invention is not restricted to optimizations of several pulses of a single scan wherein only the pulses that are applied in a single scan are optimized simultaneously. That is, in a one or two-dimensional experiment, comprising M rf pulses and N scans, MN rf pulses can be optimized. The INEPT (Insensitive Nuclei Enhanced Polarization Transfer) sequence which has been shown by Morris and Freeman (J. Am. Chem. Soc. 101 (1979) 760-762) and is a central building block of many NMR experiments, is taken as a possible application example. The INEPT sequence is used for polarization transfer between two coupled spins. The product operator formalism which has been shown by Sørensen et at (Prog. NMR Spectrosc. 16 (1983), 163-192) can be used to summarize the INEPT sequence for a two spin system according to the state of the art as follows:

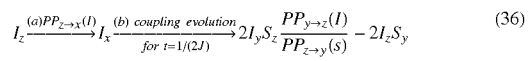

(a) starting from z magnetization, x magnetization on the I spins is created by means of a PP (point-to-point) pulse. (b) Then, for a duration that ideally is 1/(2J), coupling evolution is allowed to occur so that the antiphase operator $2I_yS_z$ evolves. (Usually, chemical shift evolution is refocused either by a 180° UR (unitary rotation) pulse on spins I and S after one half of the evolution time, namely 1/(4J). Alternatively, PP inversion pulses on I and S, respectively, after 1/(8J) and 3/(8J) can be used, as was shown by Hwang et al. (J. Magn. Reson. A 112 (1995)) and by Adams (Magn. Reson Chem. 46 (2008), 377-380). In the following, we are referring to this case.) (c) Finally, the coherence is transferred from spin I to S by means of two PP pulses. Simple rectangular pulses as well as composite and shaped pulses can be used as PP pulses.

In contrast to the state of the art, in principle, it is not necessary that all spins of a certain offset range have the same phase with respect to I at the beginning and at the end of the coupling evolution (b). It is sufficient, when both pulses before and after the coupling evolution time (b) completely transfer the initial $I_z$ operator to transversal in-phase operators having the form $I_\phi=\cos(\phi) I_x+\sin(\phi) I_y$, wherein φ can arbitrarily vary with the offset, and, if two PP(180°) pulses are used for refocusing the chemical evolution at the end of (b), the antiphase operators having the form $I_{\phi+90}°S_z=\cos(\phi+90°) 2I_xS_z+\sin(\phi+90°) 2I_yS_z$, are completely transferred to $2I_zS_z$ in a concerted manner. Thereafter, the desired antiphase coherence on spin S can be created with arbitrary phase by a conventional PP pulse on spin S.

This problem can be reduced to the case of an ensemble of uncoupled spins which can be described by the Bloch equations (Eq. (4)). We assume initial z magnetization that is initially transferred to transverse magnetization $M_\phi=\cos(\phi) M_x+\sin(\phi) M_y$ and, immediately thereafter, that transverse magnetization is rotated back to the z axis by a second pulse. (The phase difference of 90° of the antiphase operators at the end of (b) with respect to the in-phase operators at the beginning of (b) can be considered in our simplified model by addition of 90° the overall phase of the second pulse.)

In order to construct such kind of COOP pulses according to the present invention, first, we optimize a group of two COOP pulses with the following quality factor which is not obvious for a skilled person:

$$\Phi_d = M_x^{(1)}(T) \cdot M_x^{(2)}(T) - M_y^{(1)}(T) \cdot M_y^{(2)}(T), \qquad (37)$$

wherein the end-costate vectors are given by $\lambda^{(1)}(T)=(M_x^{(2)}, -M_y^{(2)}, 0)^T$ and $\lambda^{(2)}(T)=(M_x^{(1)}, -M_y^{(1)}, 0)^T$. The individual members of the two COOP pulses obtained with this quality factor both maximize transverse magnetization with the condition $$M_x^{(1)}(\nu) = M_x^{(2)}(\nu), \quad (38)$$

$$M_y^{(1)}(\nu) = -M_y^{(2)}(\nu). \quad (39)$$

That is, the final magnetization vectors of the two COOP pulses ideally are symmetric with respect to the x axis, so that the equations (38) and (39) can be summarized: $M^{(1)}(\nu) = U_x(\pi) M^{(2)}(\nu) U_x^{-1}(\pi)$, wherein the unitary transformation $U_k(\alpha) = \exp\{-i\alpha I_k\}$ corresponds to a rotation by $\alpha$ about the k axis (k is x, y or z). Accordingly, the effective propagators $W^{(j)}(\nu)$ of the individuals of the group of COOP pulses are symmetric with respect to an axis in the transverse plane, which is constant, in this exemplary case the y axis, i.e.

$$W^{(1)}(\nu) = U_y(\pi) W^{(2)}(\nu) U_y^{-1}(\pi) \quad (40)$$

because the propagators have a phase difference of 90° with respect to the final magnetization vectors.

The relationship from (J. Magn. Reson. 176 (2005)) shown by Luy et al. is used for obtaining the COOP-INEPT pulse pair according to the present invention:

$$\overline{W}^{tr}(\nu) = U_y(\pi) \overline{W}^{-1}(\nu) U_y^{-1}(\pi), \quad (41)$$

wherein $\overline{W}^{tr}(\nu)$ is the phase and time inverted propagator of the pulse W. We obtain $$\begin{aligned}\left[\overline{W}^{(1)}(\nu)\right]^{tr} &= U_y(\pi) [W^{(1)}(\nu)]^{-1} U_y^{-1}(\pi) \\ &= U_y(\pi) \{U_y(\pi) [W^{(2)}(\nu)]^{-1} U_y^{-1}(\pi)\} U_y^{-1}(\pi) \\ &= W^{(2)}(\nu)^{-1}\end{aligned} \quad (42)$$

It is easy to show that $[\overline{W}^{(2)}(\nu)]^{tr} = W^{(1)}(\nu)^{-1}$ also holds true. Thus, by time and phase inversion of one of the two individuals of the group of COOP pulses the inverse propagator of the other individual can be obtained. In order to obtain the pulse, that is needed after the evolution time (b), all that is necessary is to add 90° to the overall phase of the time and phase inverted pulse.

Without any restriction with respect to the phase, COOP-INEPT pulses can bring z magnetization to the transverse plane and back to the z axis, conferring additional degrees of freedom to the INEPT sequence and allowing for the optimization of more robust and more broadbanded pulses.

In another preferred embodiment of the invention principles of COOP-INEPT pulses are combined with the ICEBERG principle from (J. Magn. Reson 192 (2008) 335-343) in a manner that is not obvious to a person skilled in the art. Due to the equivalence of chemical shift evolution and heteronuclear coupling evolution, in this case it is sufficient to look at an ensemble of uncoupled spins at different offsets.

Conventional excitation pulses ideally create transverse magnetization with uniform phase. (For example, an ideal $PP_{z...x}$ excitation pulse rotates the magnetization from the z to the x axis for all desired offsets.) In contrast thereto, ICEBERG excitation pulses create transverse magnetization with a linear offset-dependency of the phase. The relation between the above COOP INEPT variant and its ICEBERG modification is analogous. Accordingly, in order to obtain two COOP-INEPT pulses, first, two pulses have to be optimized that create transverse magnetization, wherein the final magnetization vectors of the first and second pulse ideally lie in the transverse plane for all considered offsets and are symmetrical to each other with respect to the x axis at identical offset frequency (see above). Transverse magnetization is also created in the ICEBERG modification of the COOP-INEPT method, however, here, the final magnetization vectors for identical offsets are symmetrical with respect to an axis in the transverse plane, the phase of which linearly depends on the offset:

$$M^{(1)}(\nu) = U_\phi(\pi) M^{(2)}(\nu) U_\phi^{-1}(\pi) \quad (43)$$

wherein $U_\phi(\pi) = \exp\{-i\pi I_{(Cx+Sy)}\}$ with $C = \cos(\phi) = \cos(2\pi\nu_{off}RT)$ and $S = \sin(2\pi\nu_{off}RT)$. R is the so-called R factor as it has been defined by Gershenzon et al. in (J. Magn. Reson 192 (2008) 335-343).

In order to be able to optimize such pulses, we define the quality factor $$\Phi_\epsilon = \{M_x^{(1)}(T)M_x^{(2)}(T) - M_y^{(1)}(T)M_y^{(2)}(T)\} \cdot (C^2 - S^2) + \\ 2\{M_x^{(1)}(T)M_y^{(2)}(T) - M_y^{(1)}(T)M_x^{(2)}(T)\} \cdot (CS) \quad (44)$$

Thus, we for the final costate vectors we obtain $$\lambda^{(1)}(T) = \begin{pmatrix} (C^2 - S^2) \cdot M_x^{(2)}(T) + 2CS \cdot M_y^{(2)}(T) \\ -(C^2 - S^2) \cdot M_y^{(2)}(T) + 2CS \cdot M_x^{(2)}(T) \\ 0 \end{pmatrix} \quad (45)$$

and $$\lambda^{(2)}(T) = \begin{pmatrix} (C^2 - S^2) \cdot M_x^{(1)}(T) + 2CS \cdot M_y^{(1)}(T) \\ -(C^2 - S^2) \cdot M_y^{(1)}(T) + 2CS \cdot M_x^{(1)}(T) \\ 0 \end{pmatrix} \quad (46)$$

Like in the COOP-INEPT method already discussed above, after an optimization with this quality factor, one of the two pulses is kept unmodified and used as first COOP-INEPT-ICEBERG pulse and a second of the two pulses is phase and time inverted and used as second COOP-INEPT-ICEBERG building block.

The main difference with respect to the COOP-INEPT method discussed above resides in the fact that the in the ICEBERG variant of the optimization, the final magnetization vectors are defined such that during a time T'=RT free evolution is effective. That is, the final state after the first COOP-INEPT-ICEBERG pulse corresponds to a state after a conventional COOP-INEPT pulse and a free evolution time T'. Consequently, for the ICEBERG variant, the first free evolution time of 1/(8J) becomes shorter according to 1/(8J)−T'. (Therefore, the maximum value of T' is 1/(8J).) In analogy, the second ICEBERG pulse of our INEPT sequence has to start earlier by a time of T' as compared to a conventional COOP-INEPT pulse. Thus, one particular advantage of the ICEBERG variant of the COOP-INEPT method lies in the fact that the total duration of an ICEBERG-INEPT block is reduced by 2T' with respect to the duration of a conventional COOP-INEPT block with equal pulse durations T (see FIG. 12). Thus, an INEPT block with reduced total duration and comparably quality or equal duration and higher robustness with respect to offset and rf inhomogeneity can be created.

Figure 12:
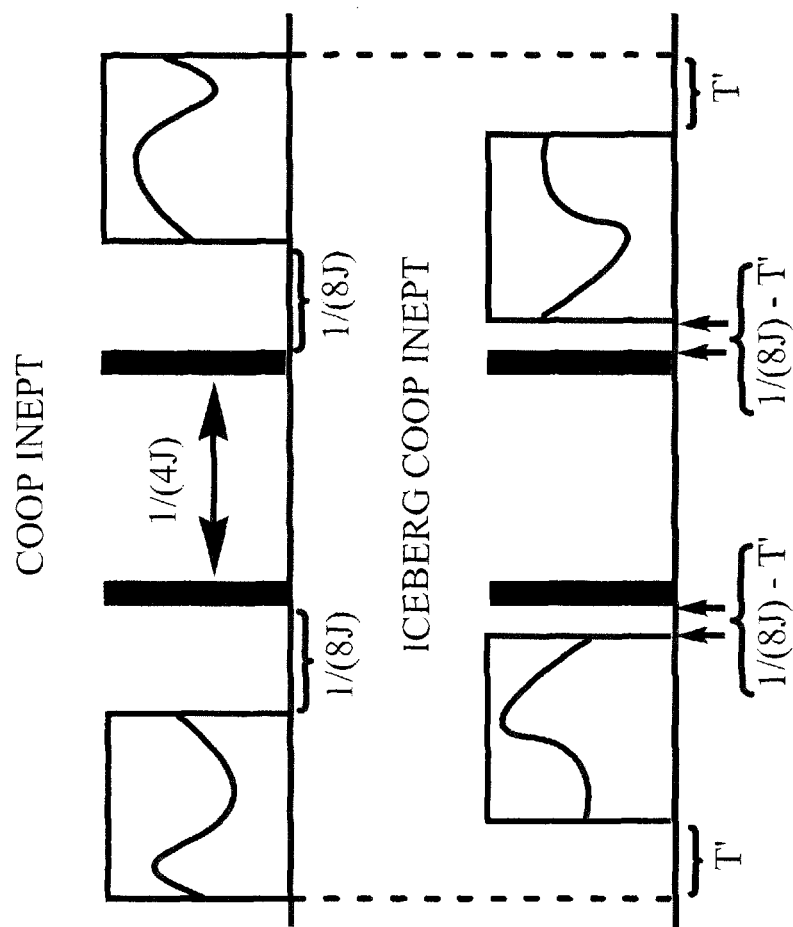
FIG. 12 shows an advantage of the COOP-INEPT application through reduction in the total duration of an ICEBERG-INEPT block.
Figure 13:
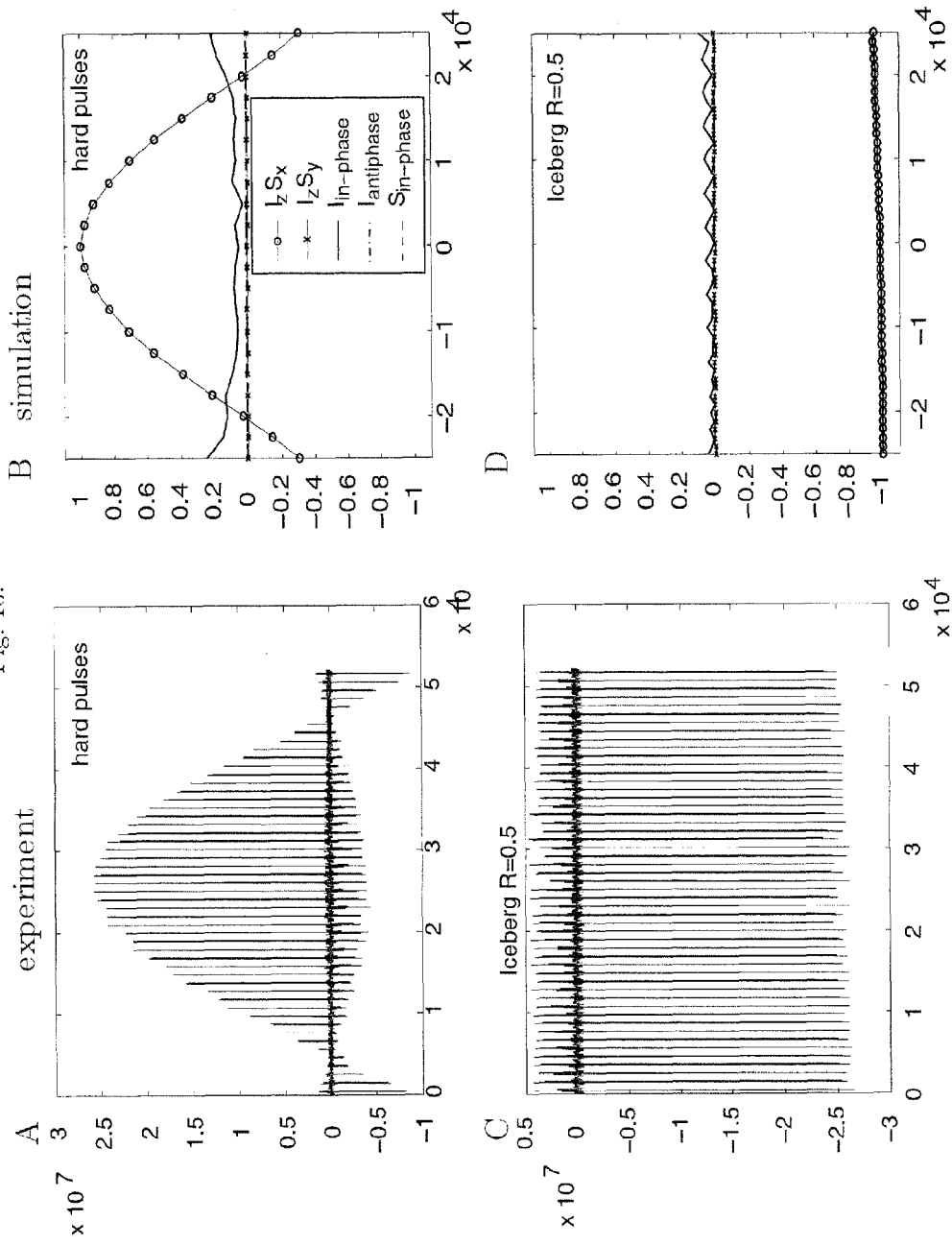
FIG. 13 shows experimental and simulated results for a COOP-INEPT-ICEBERG pulse pair.

In FIG. 13 simulated (B, D) and experimental (A, C) results of the COOP-INEPT-ICEBERG technique (C, D) are compared with the state of the art (A, B). The two tested pulse sequences are displayed in FIG. 12. The sequence according to the state of the art creates the desired anti phase magnetization for a narrow offset range while for offsets beyond ±10 kHz the coherence transfer efficiency drops down rapidly. Good coherence transfer efficiency is observed for the sequence according to the present invention.

FIG. 12 shows a comparison of the two COOP-INEPT variants. For COOP pulses of equal lengths the duration of the ICEBERG sequence is reduced by T'=RT. Only the pulse sequences for the channel on spin I are displayed. PP inversion pulses on spin S are applied simultaneously or immediately after the PP inversion pulse on spin I. After the last COOP pulse, a 90° pulse is applied on S.

FIG. 13 shows experimental (C) and simulated (D) results for a COOP-INEPT-ICEBERG pulse pair having a duration of 200 µs and a maximum rf amplitude of 10 kHz. Very good coherence transfer efficiency is observed for an offset range of 50 kHz and a robustness with respect to the if amplitude of ±5%. For comparison, experiment and simulation for rectangular pulses with T=25 µs are shown. Here, the coherence transfer efficiency rapidly drops for offset frequencies beyond ±10 kHz. The underlying pulse sequence is displayed in FIG. 12. Although the two COOP-INEPT-ICEBERG pulses are 350 µs longer than the two rectangular pulses, the total duration of the COOP-INEPT sequence is increased by only 150 µs with respect to the rectangular pulse variant (cf. FIG. 12).

The present invention is not restricted to the optimization of pulses for INEPT-like sequences.

In a preferred embodiment of the invention, pulses flanking the $t_1$ period of a NOESY-like experiment are optimized. Therein, the method is analogous to the above COOP-INEPT method, wherein here, there is no step of phase shifting the second pulse by 90°. In addition, according to the present invention, pulses flanking the $t_1$ period of a COSY-like experiment can be optimized.

The present invention relates to the concept of simultaneously optimized pulses, that act in a cooperative way, compensating each others imperfections. That is, the present invention generally relates to pulses that can have improved properties when acting together than single pulses. In particular, the present invention relates to simultaneously optimized pulses that act in a cooperative way, i.e. whose averaged effect has desired properties or whose system responses are in a certain relation to each other. That is, that in contrast to conventional approaches, the single pulses do not have to have these properties (or not in the desired quality), for example, such pulses which can compensate each other's errors in an averaging process. In the simplest case, the averaging relates to an averaging in the time dimension of the signals (FIDs) of several experiments (scans). However, no actual averaging has to be carried out, as it is the case for the COOP-INEPT sequence, and the cooperativity of the pulses resides in the fact that the respective effects of the single pulses are related in specific desired way.

Although for simplicity only examples involving uncoupled spins were considered, it is important to note that the COOP approach can also be applied to coupled spin systems. Sørensen et al. show (Prog. NMR Spectrosc 16 (1983), 163-192) how such spin systems can be described using the product operator formalism. Another method for describing coupled multi-spin systems is the density operator formalism as it was shown by Ernst et al. (Principles of nuclear magnetic resonance spectroscopy. Clarendon Press, 1987), wherein Ernst et al. also show (Principles of nuclear magnetic resonance spectroscopy, Clarendon Press, 1987), how relaxation can be taken account of in the density operator formalism. With the help of generalized optimal control based algorithms, such as the variant of the GRAPE (gradient ascent pulse engineering) algorithm according to the present invention, COOP pulses can be efficiently optimized.

Further systems and experiments to which the method according to the present invention can be applied, comprise pure quantum states, which can, for example, be described by the time-dependent Schrödinger equation as well as decoupling experiments that can, for example, efficiently be described by an equation of motion for real four-dimensional state vectors, as it has been described by Neves et al. in "Heteronuclear Decoupling by Optimal Tracking", J. Magn. Reson. 201, 7-12 (2009).

In addition, the principle of simultaneously optimizing cooperatively acting pulses according to the present invention can not only be implemented as a gradient-based method but can also be applied to other optimization methods, for example, such as Krotov methods, for example as shown by Krotov et al. (Eng. Cybern. 21, 123 (1983), Russian original: Izv. Abad. Nauk. SSSR Tekh. Kibern. 52 (1983), 152167), by Konnov et al. (Autom. Remote Control 60, 1427 (1999)), Russian original: Avtom. Telemekh, 1999, 7788), by Palao et al. (Phys. Ref. Lett. 89, 188301 (2002)) and of Palao et al. (Phys. Rev. A 68, 062308 (2003)), monotonically convergent methods, for example, as shown by Maday et al. ("New formulation of monotonically convergent quantum control algorithm", J. Chem. Phys. 118 (2003) 81918196), by Zhu et al. ("A rapid monotonically convergent algorithm for quantum optimal control over the expectation value of a finite operator" J. Chem. Phys. 09:385391, 1998), as well as combinations thereof, for example as shown by Machnes et al. (Comparing, Optimising and Benchmarking Quantum Control Algorithms in a Unifying Programming Framework", Phys. Rev. A, in press (2011)) and Eitan et al. ("Optimal control with accelerated convergence: Combining the Krotov and quasi-Newton methods", Phys. Rev. A 83, 053426 (2011)) as well as methods shown by Tannor et al. ("Time Dependent Quantum Molecular Dynamics", chapter Control of photochemical branching: Novel procedures for finding optimal pulses and global upper bounds, pages 347-360. Plenum, 1992). So far, the invention was demonstrated for the GRAPE algorithm, wherein in an iteration step scaled or non-scaled gradients are added to all controls. Also methods where in one iteration step scaled or non-scaled gradients are added to less than all controls are methods according to the present invention. Thus, for an arbitrary number of iteration steps, scaled or non-scaled gradients can be added to one or several controls, until an arbitrary convergence criterion is fulfilled or a certain number of iterations was exceeded, whereafter gradients are added to one or several controls for an arbitrary number of further iteration steps until an arbitrary convergence criterion is fulfilled or a certain number of iterations was exceeded, wherein the latter control (s) can be entirely or partly identical to or different from the control(s) of the preceding iteration steps.

The COOP method is not restricted to experiments with several scans, as was shown for the case of COOP-INEPT sequences. In experiments, wherein the different members of a group of COOP pulses are used in different scans, the COOP method can be understood as a complement and/or generalization of phase cycling as shown by Keeler, Bodenhausen, Kogler, Ernst, Bain, Levitt, Madhu and Hughes (Understanding NMR Spectroscopy, Wiley, Chichester, 2005; J. Magn. Reson. 58 (1984) 370-388; J. Magn. Reson. 56 (1984) 418-427; J. Magn. Reson. 155 (2002) 300-306), of base cycling and difference spectroscopy (for example as described in Principles of Nuclear magnetic resonance spectroscopy. Clarendon Press, 1987).

In conventional phase cycling, in every scan—despite of an overall phase difference—identical pulses are applied.

For the above case of the pulses for total elimination of magnetization the optimal group of COOP pulses also consisted of pulses that—except for an overall phase difference—were identical. Therefore, it is possible to automatically create phase cycles using the COOP method. However, it is important to note that here, it would not have been possible to find the goal of the optimization only by taking account of coherence transfer pathways. The COOP solution rather relies on the simultaneous optimization of specific pulse forms (saturation pulses), combined with the resulting simple phase cycle. As was shown here, COOP pulses do not generally differ by the overall phase.

In the presented COOP examples, a constant receiver phase was assumed. It is however simple to lift this limitation by adding an additional control for the receiver phase in order to obtain an increased flexibility as in conventional phase cycling or in difference spectroscopy.

In conventional difference spectroscopy (Ernst, Bodenhausen, Wokaun, Principles of nuclear magnetic resonance spectroscopy. Clarendon Press, 1987) different pulses are often applied in subsequent scans. However, these pulses typically are either simple rectangular pulses or are optimized for a single scan, so that the full flexibility of the COOP method disclosed herein cannot be exploited.

This has exemplarily shown for the problem of solvent suppression ("COOP-WET"). The possibility of cooperative compensation of pulse imperfections opens up new degrees of freedom for the optimization, that in total leads to better averaged properties.

The method of the present invention is not restricted in that only one pulse per scan may be replaced. Although we have shown exemplary cases where only one pulse is varied, in analogy to phase cycling, several COOP cycles can simultaneously be applied to different pulses in the sequence. Accordingly, in embodiments, where several COOP pulses are optimized for a single scan, for example like the COOP-INEPT method, it is possible do extend the optimization to several scans. Even robuster pulses can be created due to the thus obtained further degrees of freedom.

In contrast to phase cycling, the embodiments of the invention are not restricted to a global phase cycle of the pulses, but both the amplitude modulation and the phase modulation of the pulses is optimized simultaneously (including a possible frequency modulation of the pulses because the phase modulation can always be expressed as a phase modulation). In all embodiments of the invention, it is possible to selectively optimize the amplitude or phase modulation only.

The gradient-based method presented here demonstrates that the efficient simultaneous optimization also of complicated COOP pulses is possible. However, the invention is not restricted to this particular optimization method, i.e. it also extends to simultaneously optimized pulses with desired averaged and cooperative properties, respectively, that are found by other methods. Thus, Levante, Bremi and Ernst describe in J. Magn. Reson A 121 (1966) 167-177 an alternative method for the calculation of gradients.

In the embodiments of the invention where the contributions of all scans are averaged, instead of an equal weighting, the contributions of the scans can be weighted arbitrarily. This is especially of interest in applications, where no dummy scans are desired and therefore the full equilibrium magnetization is present at the beginning of the first scan, whereas at the beginning of the further scans the equilibrium magnetization is not fully re-established. Another application where this could be of relevance are experiments with hyperpolarization.

In a further embodiment of the invention, signals of the different scans for which COOP pulses have been optimized, are stored separately and are combined with each other in an arbitrary manner (e.g. different weighting), for example in order to compensate different initial magnetizations.

In a further embodiment of the invention, COOP pulses are optimized whose individual scans are differently combined with each other in order to obtain different results. In a particularly preferred embodiment of the invention, COOP pulses are optimized whose individual FIDs, for example by addition or subtraction, give a different desired result, respectively.

In a further embodiment of the invention COOP pulses are optimized so that by cycling through a COOP pulse cycle and summing up the resulting FIDs an isotope filter is obtained that selectively only suppresses or lets pass signals of protons having a direct coupling to one single isotope of a certain element, and signals of protons that are bound to another isotope of the same element are treated in the opposite way, i.e. they are allowed to pass or they are suppressed. In an experiment carried out accordingly only signals of protons show up, that are bound to the same isotope of an element. Thus, for example, signals of $^1$H-$^{13}$C groups can be suppressed but not signals of $^1$H-$^{12}$C groups, so that $^1$H-$^{13}$C signals are selectively filtered. For example, possible isotope pairs for such isotope filters are $^{13}$C/$^{12}$C and $^{15}$N/$^{14}$N, respectively.

In a further embodiment of the invention, COOP pulses are optimized, so that by cycling through a COOP pulse cycle and adding the resulting FIDs an improved multiplicity filter is obtained, as it is already been known from the DEPT sequence of Pegg and Bendall Magn. Reson. 55 (1983) 114-127). Thus, only signals of defined $^1$H$_n$-$^{13}$C groups would be visible for a value for n, whereas others would be canceled when adding the FIDs.

In a further embodiment of the invention COOP pulses are optimized so that by cycling through a COOP pulse cycle and adding the resulting FIDs an improved multi quantum filter is obtained so that only signals of a defined coherence order are allowed, whereas others are suppressed.

In a further embodiment of the invention, COOP pulses for NMR and imaging applications are optimized, so that by cycling through a COOP pulse cycle and adding the system states between two signals, maximized contrast is obtained, for example in such a way that the individual pulses create system states with opposite sign, wherein the two signals differ with respect to an arbitrary characteristic. For example, these characteristics can be $T_1$- and/or $T_2$-relaxation times, chemical shift, location in the sample, diffusion coefficient, etc.

In a further embodiment of the invention, different (but simultaneously optimized and therefore "cooperative") decoupling sequences are applied, for example in order to achieve an improved suppression of decoupling sidebands.

In a further embodiment of the invention, different (but simultaneously optimized and therefore "cooperative") pulses are applied, that by additional averaging of the resulting FIDs select defined coherence transfer pathways, but suppress other coherence transfer pathways, for example in order to obtain improved phase cycles.

In a further embodiment of the invention, different (but simultaneously optimized and therefore "cooperative") pulses are applied, representing improved excitation pulses.

In a further embodiment of the invention, pulses that can be used as multi quantum filters are optimized for a scan.

In a further embodiment of the invention, pulses that can be used as mixing pulses, for example for heteronuclear and/or homonuclear Hartmann-Hahn-transfer experiments, for example like TOCSY, are optimized for a scan.

In a further embodiment of the invention, pulses that can flank a diffusion delay are optimized for a scan.

In a further embodiment of the invention, pulses that can flank a delay for the evolution of chemical shift and/or coupling are optimized for a scan.

Preferred applications of the invention lie in the field of NMR spectroscopy but also in other spectroscopical applications, for example such as electron spin resonance or optical spectroscopy. Applications in NMR imaging with medical applications (but also with other applications, for example in material science) are possible as well, for example by slice-selective pulses or artifacts in the transition regions. Moreover, COOP pulses can find applications in quantum information processing, where this list is not limitative in scope.

Further preferred examples of use of the present invention comprise NMR and NQR ("nuclear quadrupole resonance") spectroscopy in liquid state, liquid crystalline state, and in gas phase as well as solid state NMR spectroscopy.

Further preferred examples of use of the present invention comprise NMR spectroscopy of biopolymers such as RNA, DNA, proteins and NMR spectroscopy of biomolecules.

Further preferred examples of use of the present invention comprise precision measurements, for example such as time measurements (as, for example, with atomic clocks), magnetic field measurements, magnetic gyroscopes and position determination, for example, as required for navigation.

Further preferred examples of use of the present invention comprise ion traps, quantum information processing, quantum computing, quantum communication, quantum cryptography, quantum memory, the control of quantum bits ("qubits").

A particularly preferred example of use of the present invention comprises quantitative NMR spectroscopy, for example as it is used in polymer analytics and in quality control of chemical products. "Quantitative NMR spectroscopy" comprises the high-precision determination of signal integrals for quantitative analysis of chemical substances, however, without being restricted thereto.

The method according to the present invention can also be applied in the following fields:
  ion traps
  atom traps
  atomic beam experiments
  neutron beam experiments
  solid-state qubits
  quantum dots
  nitrogen vacancy (NV) centers in diamond
  supraconducting qubits (Josephson devices Optimal control based techniques for the efficient optimization of complex COOP pulses open new avenues for pulse sequence optimization. The goal of the presented examples was to illustrate the basic concept and to point out potential applications of COOP pulses. For example, it was demonstrated that the approach may be useful for water suppression techniques such as WET. However, for practical solvent suppression, it is necessary to adjust the design criteria for the optimized COOP pulses, which would be easy to realize for a skilled person and therefore represents a further embodiment of the invention. It is also important to point out that the present algorithm for the optimization of COOP pulses can be generalized in a straightforward way to include relaxation effects. Khaneja, Reiss, Kehlet, Schulte-Herbrüggen, Glaser, Gershenzon, Kobzar, Luy and Skinner demonstrated (J. Magn. Reson. 172 (2005) 296-305; J. Magn. Reson. 188 (2007) 330-336), how relaxation effects can be taken into account in a straightforward manner. Possible examples of use of the present invention and of its embodiments comprise nuclear magnetic resonance (NMR) spectroscopy, electron spin resonance (ESR) spectroscopy, magnetic resonance (MR) imaging, microwave spectroscopy, quantum information processing, wherein this is not an enumeration limitative in scope.

On the one hand the present invention relates to a gradient based or numerical optimization method for the simultaneous optimization of an arbitrary number of N≥2 electromagnetic pulses, characterized by the following steps:

first, averaging of the individual system states that are created by the electromagnetic pulses and that are described with a formalism for the description of spin systems, comprising the Bloch equations, the density operator formalism, the product operator formalism, and the modifications of these formalisms for taking relaxation and radiation damping, respectively, into account, in order to eliminate undesired single contributions of the system states and to obtain desired single contributions of the system states and an optional second step, in which the individual system states, created by the pulses, do not have to correspond to the physical final states of the system and are modified, following the optimization described in the first step, by further operations, comprising time- and/or phase-inversion and/or an overall phase shift.

On the other hand, the invention relates to a gradient based or numerical met hod for the simultaneous optimization of an arbitrary number N≥2 of electromagnetic pulses, characterized by the following steps:

first, in that the individual system states that are created by the electromagnetic pulses and that are described with a formalism for the description of spin systems, comprising the Bloch equations, the density operator formalism, the product operator formalism, and the modifications of these formalisms for taking relaxation and radiation damping, respectively, into account, are symmetry-related with respect to an axis in the transverse plane, whose phase is constant or linearly dependent on offset or in that the single contributions of the system states have opposite signs (maximum contrast)

and an optional second step, in which the individual system states, created by the pulses, do not have to correspond to the physical final states of the system and are modified, following the optimization described in the first step, by further operations, comprising time- and/or phase-inversion and/or an overall phase shift.

We claim:

1. A method for simultaneous optimization of a group of N electromagnetic pulses $P^{(j)}$ with N>1, wherein the pulses are used for manipulation of system states of a spin system using an optimal control based algorithm, the method comprising the steps of:
  a) choosing N electromagnetic initial pulses $P^{(j)}$ having a duration $T^{(j)}$ and with controls $v_x^{(j)}(t)$ and $v_y^{(j)}(t)$, wherein $j \in \{1, 2, \ldots, N\}$ and t is a time variable running between 0 and the duration $T^{(j)}$ of each pulse $P^{(j)}$;
  b) calculating N trajectories of the system states of the spin system experiencing the pulses $P^{(j)}$ using quantum mechanical equations of motion, wherein a given respective initial state is assumed;
  c) defining a quality factor $\phi$ that is at least dependent on final system states at a point in time $T^{(j)}$ and that takes into account elimination of undesired single contributions of the system states and obtaining desired single contributions of the system states;

d) calculating costates $\lambda^{(j)}(T^{(j)})$;

e) calculating N trajectories of the costates $\lambda^{(j)}(t)$ for $0 \leq t \leq T^{(j)}$;

f) calculating gradients of the quality factor $\phi$ with respect to the controls $v_x^{(j)}(t)$ and $v_y^{(j)}(t)$ for an arbitrary number of points in time;

g) adding gradients to the controls $v_x^{(j)}(t)$ and $v_y^{(j)}(t)$, thereby obtaining updated controls $v_x^{(j)}(t)$ and $v_y^{(j)}(t)$;

h) repeating steps b) to g) using the updated controls $v_x^{(j)}(t)$ and $v_y^{(j)}(t)$ until a defined completion criterion is fulfilled; and i) implementing the electromagnetic pulses following step h).

2. The optimization method of claim 1, wherein in step f), the gradients of the quality factor $\phi$ are calculated for each point in time t.

3. The optimization method of claim 1, wherein the system states of the spin system are described by magnetization vectors $M^{(j)}(t)$ so that, in step b), trajectories of the magnetization vectors $M^{(j)}(t)$ are calculated for $0 \leq t \leq T^{(j)}$ using Bloch equations, wherein the quality factor $\phi$ depends on final magnetization vectors $M^{(j)}(T^{(j)})$ and, in step e), calculation of the trajectories of costate vectors $\lambda^{(j)}(t)$ for $0 \leq t \leq T^{(j)}$ using equations of motion for the costate vectors is carried out according to:

$$\dot{\lambda} = 2\pi v_e(t) \times \lambda(t),$$

and, in step f), calculation of the gradients of the quality factor $\phi$ is carried out by calculating x and y components of a vector product $M^{(j)}(t) \times \lambda^{(j)}(t)$:

$$\frac{\partial \Phi}{\partial v_x^{(j)}(t)} = M_y^{(j)}(t)\lambda_z^{(j)}(t) - M_z^{(j)}(t)\lambda_y^{(j)}(t)$$

$$\frac{\partial \Phi}{\partial v_y^{(j)}(t)} = M_z^{(j)}(t)\lambda_x^{(j)}(t) - M_x^{(j)}(t)\lambda_z^{(j)}(t),$$

wherein $v_e(t)$ is an effective field vector defined in terms of x and y components $v_x(t)$ and $v_y(t)$ of a control field and an offset frequency $v_{off}$, wherein $$v_e(t) = (v_x(t), v_y(t), v_{off})^t$$

and $M^{(j)}_x$, $M^{(j)}_y$, and $M^{(j)}_z$ are x, y, and z components of a time-dependent magnetization vector $M^{(j)}(t)$ that is associated with a j-th pulse $P^{(j)}$ with $\lambda^{(j)}_x$, $\lambda^{(j)}_y$, and $\lambda^{(j)}_z$ being x, y, and z components of a time-dependent costate vector $\lambda^{(j)}(t)$ that is associated with a j-th pulse $P^{(j)}$.

4. The method of claim 1, wherein the system states are described using a density operator formalism, a product operator formalism or by modifications of those formalisms for taking relaxation or radiation damping into account.

5. The optimization method of claim 1, wherein gradient information calculated in step f) is used in algorithms having a method of steepest descent.

6. The optimization method of claim 1, wherein the gradients calculated in step f) are scaled by applying a conjugated-gradient or a quasi-Newton method, and those scaled gradients are added to the controls $v_x^{(j)}(t)$ and $v_y^{(j)}(t)$ in step g).

7. The optimization method of claim 1, wherein pulses in subsequent scans are to be applied at a single position of a pulse sequence and the quality factor $\phi$ depends on an average value of the system states.

8. The optimization method of claim 7, wherein contributions of the scans to the average value are weighted.

9. The optimization method of claim 1, wherein the pulses are to be applied at different positions in a single scan of a pulse sequence and the system states are symmetry related with respect to an axis in a transverse plane.

10. The optimization method of claim 9, wherein a symmetry axis in the transverse plane has a uniform phase or a phase that linearly depends on an offset.

11. The optimization method of claim 9, wherein the pulses $P^{(j)}$ are pulses creating transverse magnetization.

12. The optimization method of claim 1, wherein the quality factor $\phi$ exclusively depends on final system states.

13. The method of claim 4, wherein the pulses serve for manipulating system states of coupled spin systems.

14. The optimization method of claim 13, wherein the pulses are heteronuclear or homonuclear decoupling pulses for suppressing heteronuclear or homonuclear coupling evolution.

15. The optimization method of claim 14, wherein decoupling pulses are divided into $N_{acq}$ acquisition points and the quality factor $\phi$ depends on the system states at times $T^k$ of the $N_{acq}$ acquisition points of all N pulses, wherein $T^k$ specifies times of acquisition points during decoupling pulses.

16. The optimization method of claim 13, wherein different decoupling pulses are provided for subsequent scans.

17. Use of the optimization method of claim 1 in the field of NMR spectroscopy, MRI, electron spin resonance spectroscopy or in optical spectroscopy.

* * * * *